US008329027B2

(12) United States Patent
Kubo

(10) Patent No.: US 8,329,027 B2
(45) Date of Patent: Dec. 11, 2012

(54) TREATMENT APPARATUS, SOLUTION STIRRING METHOD AND SOLUTION TRANSFER METHOD

(75) Inventor: Wataru Kubo, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 728 days.

(21) Appl. No.: 11/948,372

(22) Filed: Nov. 30, 2007

(65) Prior Publication Data

US 2008/0277275 A1 Nov. 13, 2008

(30) Foreign Application Priority Data

Dec. 6, 2006 (JP) ................................ 2006-329350

(51) Int. Cl.
*G01N 33/487* (2006.01)
*B01F 13/08* (2006.01)

(52) U.S. Cl. ......................... 205/799; 205/792; 366/273

(58) Field of Classification Search ........... 435/4-40.52, 435/287.1-288.7; 204/403.01-403.15; 205/777.5, 205/778, 792, 799; 436/62-71, 500-548; 422/99, 100; 366/273
See application file for complete search history.

(56) References Cited

U.S. PATENT DOCUMENTS

| | | | | |
|---|---|---|---|---|
| 5,788,819 | A * | 8/1998 | Onishi et al. | 205/155 |
| 6,342,071 | B1 * | 1/2002 | Pless | 623/3.1 |
| 2003/0118453 | A1 * | 6/2003 | Fritsch et al. | 417/48 |
| 2003/0134316 | A1 | 7/2003 | Tashiro et al. | |
| 2006/0207883 | A1 * | 9/2006 | Koval et al. | 204/518 |

FOREIGN PATENT DOCUMENTS

| | | |
|---|---|---|
| JP | 2002-371954 A | 12/2002 |
| JP | 2003-248008 A | 9/2003 |

OTHER PUBLICATIONS

Eugenii Katz, et al., Magnetic Field Effects on Bioelectrocatalytic Reactions of Surface-Confined Enzyme Systems: Enhanced Performance of Biofuel Cells, American Chemical Society, 2005, vol. 127, No. 11, pp. 3979-3988.

* cited by examiner

*Primary Examiner* — Kaj K Olsen
*Assistant Examiner* — Susan D Leong
(74) *Attorney, Agent, or Firm* — Fitzpatrick, Cella, Harper & Scinto

(57) ABSTRACT

The electrolytic reaction of a solution supplemented with oxidation-reduction substances is caused in a magnetic field. Lorentz force generated by the interaction between an electrolytic current and the magnetic field is utilized. As a result, the effective stirring or transfer of a solution as well as the detection of a biologically relevant substance with high precision can be achieved without causing the aggregation or uneven distribution of magnetic beads or the like.

4 Claims, 12 Drawing Sheets

TREATMENT APPARATUS, SOLUTION STIRRING METHOD AND SOLUTION TRANSFER METHOD

BACKGROUND OF THE INVENTION

1. Field of the Invention

The present invention relates to a solution stirring or transfer method for stirring or transferring a solution by Lorentz force generated by the interaction between an electric current generated through electrochemical reaction and a magnetic field. The present invention also relates to a treatment apparatus for efficiently performing at least one of the detection of a biologically relevant substance and the transfer of a solution using this stirring or transfer.

2. Description of the Related Art

In recent years, significantly evolving life science has required processing an enormous amount of information typified by genomes with a high throughput at a high speed. Against this backdrop, DNA or protein analysis techniques using micromachined DNA or protein chips have been established.

In this context, to hybridize target DNAs to probe DNAs in a DNA chip, a trace amount of a sample containing targets is added dropwise to an array of the DNA chip. Similarly, to immune-react target antigens with antibody probes in a protein chip, a sample is added dropwise to an array of the protein chip. Then, sufficient hybridization or antigen-antibody reaction must occur in the DNA or protein chip. Thus, the acquirement of reliable hybridization or immune reaction results requires lengthening a hybridization or antigen-antibody reaction time or promoting hybridization or immune reaction.

Examples of general approaches for promoting chemical reaction include the following two approaches: (1) an approach by which a reaction rate is improved; and (2) an approach by which the collision frequency of a substrate involved in reaction is improved.

Examples of specific methods for conducting these two approaches include the following methods: (1) a rise in reaction temperature and the addition of a catalyst; and (2) improvement in reaction temperature, an increase in substrate concentration and improvement in stirring strength.

In this context, the possible methods for promoting the general chemical reaction might be applied to hybridization or immune reaction. In such a case, the rise in reaction temperature incurs DNA dissociation in hybridization. Alternatively, this rise in reaction temperature incurs protein denaturation in immune reaction. Thus, this method did not simply serve as a reaction promotion unit. The same holds true for the other methods such as the addition of a catalyst and an increase in substrate concentration.

Thus, a promising method as a reaction promotion unit is the stirring or transfer of a solution. However, the DNA or protein chip is constructed in the form of a microcontainer array. Therefore, it was impossible to directly apply thereto a conventional stirring or transfer method using a stirrer or stirring blade. Thus, Patent Document 1 discloses a method for stirring a reaction solution in this microcontainer. Specifically, Patent Document 1 discloses a method comprising applying a magnetic field from outside to magnetic beads contained in a reaction solution.

For DNA or protein analysis, it has heretofore been demanded to establish a technique for stably transferring a solution in a very small area. Furthermore, the utilization of a microchannel in DNA or protein chips has been studied actively for the purpose of achieving a decrease in sample amount, reduction in treatment time and a high throughput. Thus, Patent Document 2 discloses a method for transferring a fluid in a capillary channel.

On the other hand, electrochemical reaction in a magnetic field generally generates Lorentz force by the interaction between an electrolytic current generated through the electrochemical reaction and the magnetic field. This Lorentz force causes a solution flow. Effects produced by this Lorentz force are called MHD (MagnetoHydroDynamic) effects and have been studied in various ways in recent years. In electrochemical reaction, this flow increases or decreases substrate supply to electrode surface. As a result, changes in electric current value are observed. For example, Katz et al. have reported the enhanced properties of biofuel cells utilizing MHD effects (Non-Patent Document 1).

(Patent Document 1) Japanese Patent Application Laid-Open No. 2003-248008

(Patent Document 2) Japanese Patent Application Laid-Open No. 2002-371954

(Non-Patent Document 1) J. Am. Chem. Soc. 2005, 127, p. 3979-3988

Patent Document 1 discloses a method for stirring a reaction solution using magnetic beads contained in the reaction solution, as described above. These magnetic beads allow the reaction solution to flow by a magnetic field changed from outside so as to stir the reaction solution. However, this stirring using the magnetic beads causes the aggregation of the magnetic beads or causes the uneven distribution of the magnetic beads depending on a container shape, an application pattern of the magnetic field and the dynamic properties of the magnetic beads. Therefore, it was difficult to perform effective and stable stirring.

Patent Document 2 discloses a method comprising introducing a magnetic fluid to a capillary channel so as to allow the magnetic fluid to occupy the whole cross section of the channel in the partial region of the channel, and transferring, in this state, the fluid in this channel by magnetism imparted from outside. However, for the construction disclosed in Patent Document 2, it was difficult to transfer the magnetic fluid stably and efficiently in the state that allows the magnetic fluid to occupy the whole cross section of the channel. It was also difficult to continue, in a solution, the stable dispersion of a ferromagnetic solid used as a magnetic fluid.

Thus, in the previous techniques, magnetic substances dispersed in a solution are controlled for stirring or transfer by the control of outside magnetic force. Therefore, a great challenge for the techniques was to maintain the dispersion stability of the magnetic substances. In this context, the present inventor has found that such dispersion stability does not have to be considered if substances for causing the solution flow are already dissolved in the solution.

SUMMARY OF THE INVENTION

Specifically, in the present invention, a voltage is applied between electrodes (cathode and anode) provided in a container, while a magnetic field is applied in a predetermined direction from outside. Then, oxidation-reduction substances added to a solution are allowed to flow by Lorentz force generated by the interaction between an electric current (flow of the oxidation-reduction substances) generated in the solution and the magnetic field. Thus, an objective of the present invention is to provide an apparatus or a method for this purpose. The present invention can cause a flow of the whole solution by such a flow of the oxidation-reduction substances.

The detection of a biologically relevant substance as well as the transfer of a solution can be achieved efficiently by utilizing this flow.

The present invention is directed to a treatment apparatus for performing at least one of the detection of a biologically relevant substance and the transfer of a solution, comprising: a container; a plurality of electrodes provided in the container; and an oxidation-reduction substance-containing solution introduced in the container, wherein the treatment apparatus performs the at least one of the detection of a biologically relevant substance and the transfer of a solution by Lorentz force generated by the interaction between an electric current generated by an electric potential or voltage applied from outside to the electrodes and a magnetic field applied from outside.

The treatment apparatus can comprise a plurality of the containers and further contains DNA as a reactive substance. The biologically relevant substance can be DNA.

The treatment apparatus can comprise a plurality of the containers and further contain an antibody as a reactive substance. The biologically relevant substance can be a protein.

In the treatment apparatus, a reactive substance can be immobilized in the container via a solid material so as to introduce the reactive substance in the container.

The present invention is directed to a treatment apparatus for performing at least one of the detection of a biologically relevant substance and the transfer of a solution, comprising: a thin tube; a plurality of electrodes provided in the thin tube; and an oxidation-reduction substance-containing solution introduced in the thin tube, wherein the treatment apparatus performs the at least one of the detection of a biologically relevant substance and the transfer of a solution by Lorentz force generated by the interaction between an electric current generated by an electric potential or voltage applied from outside to the electrodes and a magnetic field applied from outside.

The present invention is directed to a stirring method for stirring a solution in a container, comprising: preparing a container having a plurality of electrodes; introducing an oxidation-reduction substance-containing solution into the container; and stirring the solution in the container by Lorentz force generated by the interaction between an electric current generated by an electric potential or voltage applied from outside to the electrodes and a magnetic field applied from outside.

The present invention is directed to a transfer method for transferring a solution in a thin tube, comprising: preparing a thin tube having a plurality of electrodes; introducing an oxidation-reduction substance-containing solution into the thin tube; and transferring the solution in the thin tube by Lorentz force generated by the interaction between an electric current generated by an electric potential or voltage applied from outside to the electrodes and a magnetic field applied from outside.

In the present invention, electrodes are placed in a container, and oxidation-reduction substances are added to a solution in the container. Then, Lorentz force is generated by the interaction between an electric current attributed to the electrode reaction of the oxidation-reduction substances caused by a voltage (applied from outside between the electrodes) and a magnetic field applied from outside. This Lorentz force, which eventually acts on the solution, is utilized. As a result, the solution is stirred or transferred. Simultaneously therewith, the collision frequency between a reactive substance, if any, in the solution, and a biologically relevant substance is increased. Therefore, the reaction between these substances can be promoted so as to improve the detection precision of the biologically relevant substance.

According to the present invention, Lorentz force can be generated by the interaction between an electrolytic current of oxidation-reduction substances (electric current attributed to the electrode reaction of oxidation-reduction substances) in a solution and a magnetic field so as to cause a solution flow in a container. As a result, the solution can be stirred or transferred. Moreover, the collision frequency between a reactive substance, if any, in the solution, and a biologically relevant substance is increased. Therefore, the reaction between these substances can be promoted so as to improve the detection precision of the biologically relevant substance.

The present invention can provide a method for stirring a solution in a container by Lorentz force generated by the interaction between an electrolytic current of oxidation-reduction substances in the solution and a magnetic field. The present invention can also provide a method for transferring a fluid in a channel (thin tube or container) in a predetermined direction by Lorentz force generated by the interaction between an electrolytic current of oxidation-reduction substances in the solution and a magnetic field.

Further features of the present invention will become apparent from the following description of exemplary embodiments with reference to the attached drawings.

DESCRIPTION OF THE EMBODIMENTS

Next, exemplary embodiments of the present invention will be described in detail.

1. Treatment Apparatus

A treatment apparatus of the present invention can perform any of the following treatments: (1) the detection of a biologically relevant substance by the stirring of a solution using a reactive substance that specifically reacts with the biologically relevant substance; (2) the transfer of a solution; and (3) the transfer of a solution as well as the detection of a biologically relevant substance using a reactive substance that specifically reacts with the biologically relevant substance.

This treatment apparatus includes a cathode, an anode, a voltage application unit, a magnetic field application unit, a solution, and a container.

The number of each of the cathode and the anode provided therein may be one or more. The treatment apparatus may include a single cathode and a single anode or may include a plurality of cathodes and a plurality of anodes. Alternatively, one of the cathode and the anode may be a single electrode, and the other electrode may be a plurality of electrodes.

In this context, the solution contains oxidation-reduction substances. For example, a particular voltage or electric potential is applied between the cathode and the anode. As a result, reduced and oxidized forms in this oxidation-reduction substance-containing solution are consumed through oxidation and reduction reactions at the anode and the cathode, respectively, leading to a local decrease in concentration. Along with this decrease in concentration, the oxidation-reduction substances are diffusively moved from the neighboring part of the electrode to the electrode surface.

Figure 1:
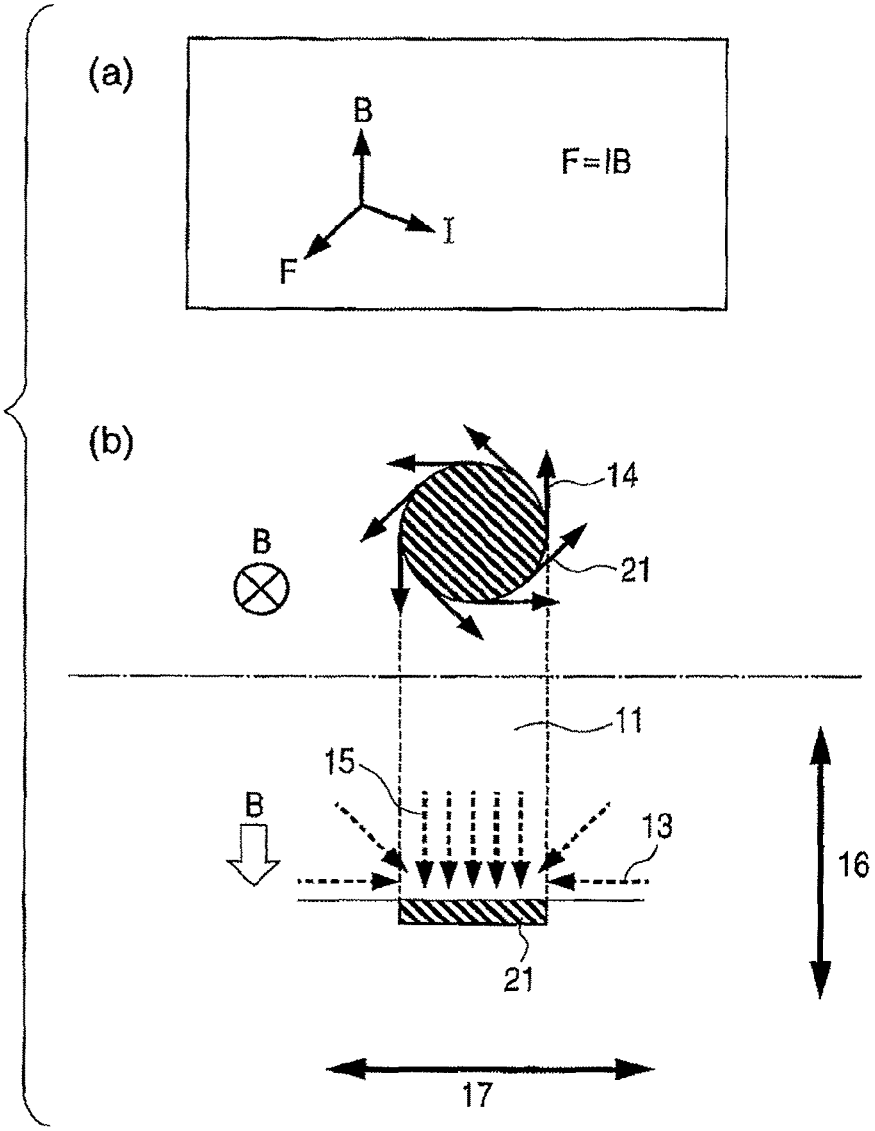
FIG. 1 is a diagram illustrating the principle of generation of force that causes a solution flow according to the present invention.

The direction of movement of the oxidation-reduction substances is greatly influenced by the shape, size and placement of electrodes. For example, each of the cathode and the anode may be a single large planar electrode constituting the inner wall of the container, and the cathode and the anode may be placed so that these electrodes face each other. Assuming such a case, oxidized and reduced forms are consumed through reactions at the cathode and the anode, respectively, leading to a local decrease in concentration. Along with this decrease in concentration, the oxidized and reduced forms are diffused in a direction in which the cathode and the anode face each other (hereinafter, this direction in which the cathode and the anode face each other is referred to as a "facing direction"). In this context, as illustrated in FIG. 1(*a*), a magnetic field is applied in a direction perpendicular to the direction of diffusion of the oxidation-reduction substances. As a result, Lorentz force eventually acts on the solution by the interaction between an electrolytic current and the magnetic field. The strength of this Lorentz force is proportional to the strength of a magnetic field and the magnitude of an electric current flowing between the cathode and the anode.

One of the electrodes (cathode and anode) may be a single large planer electrode constituting the inner wall of the container, and the other electrode may be a planar electrode smaller than that electrode. Furthermore, these two electrodes may be placed so that the electrodes face each other. In this example, a flow of the oxidation-reduction substances occurs from various directions to the planer electrodes. FIG. 1(*b*) is a side view depicting flows of the oxidation-reduction substances flowing toward this smaller planar electrode. As illustrated in the side view of FIG. 1(*b*), the flows of the oxidation-reduction substances include a flow in a direction 17 perpendicular to the facing direction. The flows of the oxidation-reduction substances in the other directions (except for the flow of the oxidation-reduction substances in a direction parallel with the facing direction) have components of the flow in the direction 17 perpendicular to the facing direction. Therefore, the application of a magnetic field in a direction 16 parallel with the facing direction can generate Lorentz force in the direction 17 perpendicular to the facing direction.

The treatment apparatus of the present invention can cause a flow in a solution, as described above, so as to stir or transfer the whole solution. A reactive substance may be contained in the solution. In such a case, the reactive substance and a biologically relevant substance can effectively be collided and reacted with each other for such stirring or transfer of a solution so as to improve the detection precision of the biologically relevant substance.

In the treatment apparatus of the present invention, the shape, size and placement of electrodes are very important, as described above, for causing a stirring or transfer flow at an effective rate in an effective direction in a solution. Hereinafter, the relationship between the shape, size and placement of electrodes and a solution flow will be shown with specific treatment apparatuses as examples.

(1) First Embodiment

Figure 2:
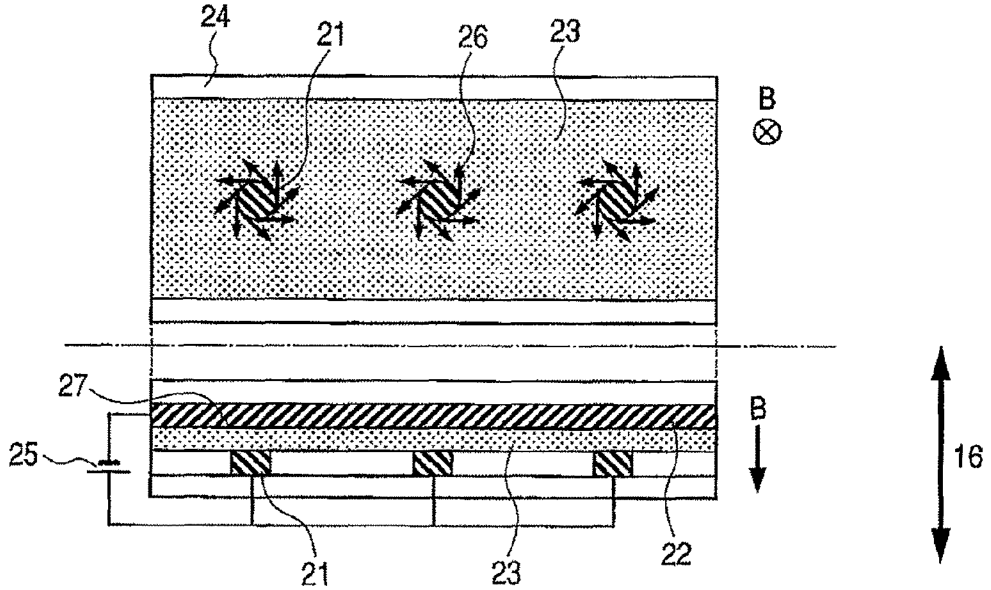
FIG. 2 is a schematic diagram depicting one example of placement of electrodes in a treatment apparatus of the present invention.

FIG. 2 illustrates one embodiment of a treatment apparatus of the present invention and illustrates an example of placement of electrodes for stirring a solution in a container. In the drawing, a direct-current power supply is used. However, an actual power supply is not limited thereto.

FIG. 2 illustrates a construction including a plurality of planar circular electrodes 21 placed alongside and a single plate electrode 22 facing the circular electrodes 21. In this construction, a solution 23 is retained between these electrodes 21 and 22 by an outer frame 24. This plate electrode 22 constitutes the whole part of one inner wall 27 of the container.

In this context, the solution contains oxidation-reduction substances. Therefore, a positive electric potential capable of oxidizing reduced forms in the solution and a negative electric potential capable of reducing oxidized forms in the solution are applied by a power supply 25 to the circular electrodes 21 and the plate electrode 22, respectively. As a result, oxidation and reduction reactions proceed at the circular electrodes 21 and the plate electrode 22, respectively.

In this procedure, a flow of the reduced forms caused toward the circular electrodes 21 displays a profile illustrated in the side view of FIG. 1. Specifically, the reduced forms present in the solution move from the neighboring parts of the electrodes and from above toward the circular electrodes 21. These flows include the flow 13 of the oxidation-reduction substances in the direction 17 perpendicular to the facing direction 16. The flows of the oxidation-reduction substances in the other directions (except for the flow of the oxidation-reduction substances in a direction parallel with the facing direction 16) contain components of the flow of the oxidation-reduction substances in the direction 17 perpendicular to the facing direction 16. In this context, the flow 13 of the oxidation-reduction substances may have components orthogonal to a magnetic field. In such a case, Lorentz force that causes a solution flow is generated. Therefore, the application of a magnetic field in a direction (direction parallel with the facing direction) 16 illustrated in FIG. 1(*b*) can generate Lorentz force in the direction 17 perpendicular to the facing direction 16 by the interaction between an electrolytic current attributed to the flow of the oxidation-reduction substances in the direction 13 or the components of this flow and the magnetic field.

Now referring to the container as a whole, force 26 that causes a solution flow illustrated by the arrows in the upper diagram of FIG. 2 is generated at each electrode, as illustrated in FIG. 2, by the interaction with a magnetic field applied toward the electrode from above (indicated as B in the drawing). As a result, a solution flow rotating around the circular electrode in a counterclockwise direction viewed from above is generated. The solution is stirred by this flow.

In this context, a reactive substance that reacts with the biologically relevant substance may be contained in this solution. In such a case, the collision frequency between the reactive substance and the biologically relevant substance is increased by the stirring. As a result, the reaction between these substances can be promoted so as to improve the detection precision of the biologically relevant substance.

Meanwhile, such application of a magnetic field causes flows of the oxidation-reduction substances toward the circular electrodes 21. Among these flows, the flow 15 in a direction parallel to the facing direction 16 is parallel to the direction of the magnetic field. Thus, the flow of the oxidation-reduction substances in this direction does not generate Lorentz force.

In the descriptions of FIGS. 1 and 2, the circular electrodes 21 are used as anodes, while the plate electrode 22 is used as a cathode. However, the circular electrodes 21 and the plate electrode 22 may be used as cathodes and as an anode, respectively. In this case, a solution flow rotating in a reverse direction of the rotation of FIG. 2 is caused in the solution.

(2) Second Embodiment

Figure 3:
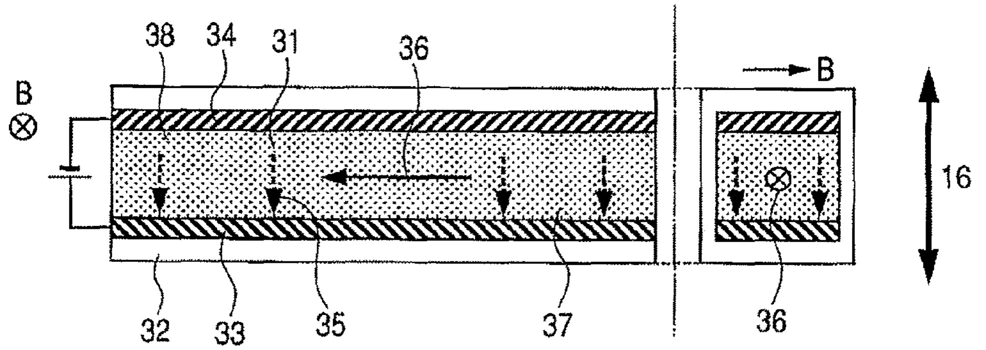
FIG. 3 is a schematic diagram depicting one example of placement of electrodes in a treatment apparatus of the present invention.

FIG. 3 illustrates another embodiment of a treatment apparatus of the present invention and illustrates an example of placement of electrodes for moving (transferring) a solution in parallel in a container. In the description of FIG. 3, a direct-current power supply is used for illustrative purposes. However, an actual power supply is not limited thereto.

FIG. 3 illustrates a construction including two planar electrodes (a planar anode 33 and a planar cathode 34) facing each other. These electrodes are placed as upper and lower electrodes in a thin tube having a square cross section. In this construction, a solution 31 is retained between these electrodes by an outer frame 32. The planar anode 33 and the planar cathode 34 constitute the whole parts of a second inner wall 37 of the thin tube and a third inner wall 38 thereof, respectively.

In this context, the solution contains oxidation-reduction substances. A positive electric potential capable of oxidizing reduced forms in the solution and a negative electric potential capable of reducing oxidized forms in the solution are applied to the lower planar electrode 33 and the upper planar electrode 34, respectively. As a result, oxidation and reduction reactions proceed at the lower and upper electrodes, respectively. In this procedure, a flow 35 of the reduced forms caused toward the lower electrode displays a profile illustrated by the dotted-line arrows in FIG. 3. In this context, the flow of the oxidation-reduction substances may have components orthogonal to a magnetic field. In such a case, Lorentz force that eventually causes a solution flow is generated. Therefore, a magnetic field (indicated as B in the drawing; direction perpendicular to the facing direction 16) is applied from the front side of the sheet toward the back side thereof in the side view (left diagram) of FIG. 3. As a result, Lorentz force eventually acts on the solution in a direction of the normal arrows in the side view of FIG. 3 (direction from the front side of the sheet toward the back side thereof in the cross-sectional view (right diagram) of FIG. 3) by the interaction between an electrolytic current and the magnetic field. Along therewith, force 36 that causes a flow of the whole solution is generated so as to efficiently transfer the solution.

In this placement of electrodes, force that causes a solution flow in the same direction as above is generated in the reaction of the upper electrode in the same manner as in the reduced forms. As a result, a flow that moves the solution in parallel in a direction from the right to the left in the side view of FIG. 3 (direction from the front side of the sheet toward the back side thereof in the cross-sectional view (right diagram) of FIG. 3) is generated so as to efficiently transfer the solution.

In this context, a reactive substance that reacts with the biologically relevant substance may be contained in this solution. In such a case, the collision frequency between the reactive substance and the biologically relevant substance is increased by the transfer. As a result, the reaction between these substances can be promoted so as to improve the detection precision of the biologically relevant substance. Alternatively, a thin tube in which the transfer of a solution is relatively difficult as compared with usual tubes may be used. In such a case, force that transfers the solution can be imparted thereto efficiently.

In the descriptions of FIG. 3, the planar electrode 33 is used as an anode, while the planar electrode 34 is used as a cathode. However, the planar electrode 33 and the planar electrode 34 may be used as a cathode and as an anode, respectively. In this case, a flow that transfers the solution in a reverse direction of the direction of FIG. 3 is caused in the solution.

Hereinafter, each member constituting the treatment apparatus of the present invention will be described in detail.

(Container)

The number of the container in the treatment apparatus of the present invention may be one or may be two or more. The treatment apparatus can include the desired number of a container with the desired size according to a target to be detected or treated in the treatment apparatus. The treatment apparatus of the present invention can be prepared as a microchip or microarray equipped with a plurality of containers. For example, the treatment apparatus is provided with a plurality of containers each containing DNA contained (introduced) as a reactive substance in a solution and is configured to be capable of detecting DNA (biologically relevant substance) through hybridization. The treatment apparatus thus configured can be used as a DNA chip or DNA microarray. Alternatively, the treatment apparatus is provided with a plurality of containers each containing an antibody contained (introduced) as a reactive substance in a solution and is configured to be capable of detecting a protein (biologically relevant substance) through antigen-antibody reaction. The treatment apparatus thus configured can be used as a protein chip or protein microarray.

(Reactive Substance)

In the present invention, a reactive substance that specifically reacts with the biologically relevant substance so as to provide for the detection of the biologically relevant substance may be contained in advance in the container. Such a reactive substance contained in the container can effectively achieve the detection of a biologically relevant substance. The reactive substance is contained in advance in the solution or immobilized in the container so as to introduce the reactive substance in the container. Examples of the reactive substance can include those specifically reacting with the biologically relevant substance. Specific examples thereof can include antibodies, DNA fragments, RNA fragments, DNA, RNA and substances that react with particular proteins.

These reactive substances may be immobilized on a solid material provided in the container. This solid material is not particularly limited and may be an electrode, the inner wall of the container or a special material provided for immobilizing the reactive substance.

For example, a glass or plastic material constituting a reaction cell may be used as the solid material. Alternatively, a glass fiber, a filter (e.g., cellulose) or fine particles may be used as the solid material. Examples of such a solid material in the fine particle form can include fine particles of biological origin, inorganic fine particles and organic fine particles. Examples of the fine particles of biological origin include erythrocytes and bacteria (e.g., staphylococci and streptococci) dispersed by treatment. Examples of the inorganic fine particles include silica, alumina and bentonite. Examples of the organic fine particles include homopolymers and/or copolymers of vinyl monomers such as styrene, vinyl chloride, acrylonitrile, vinyl acetate, acrylic esters and methacrylic esters. Alternative examples of the solid material include fine particles of butadiene copolymers (e.g., styrene-butadiene copolymers and methyl methacrylate-butadiene copolymers) and a liposome having a lipid bilayer.

In the present invention, to immobilize the reactive substance onto the surface of the solid material, for example, the following methods known in the art can be utilized: (1) an ionic bond method; (2) a physical adsorption method; and (3) a covalent bond method.

The ionic bond method (1) causes the electrostatic bond between the reactive substance such as a protein, DNA or RNA and the solid material surface. This approach allows bonding reaction to easily proceed between the reactive substance and the solid material. However, the bonding power between the solid material and the reactive substance is weak.

The physical adsorption method (2) is a bonding method that utilizes, for example, the hydrophobic bond between a hydrophobic portion of the solid material surface and a hydrophobic portion of a protein (reactive substance). The physical adsorption method allows bonding reaction to easily proceed between the reactive substance and the solid material. However, the bonding power between the solid material and the reactive substance is weak.

The covalent bond method (3) causes the covalent bond between the solid material surface and the reactive substance via a highly reactive functional group bound with at least one of the solid material surface and the reactive substance. This approach produces a strong bonding power. Examples of a functional group (a) that can be introduced into the reactive substance so as to bind the solid material with the reactive substance by the covalent bond method can include the following groups.

A free amino, hydroxyl, phosphate or carboxyl group, a cysteine sulfhydryl group, a histidine imidazole group, a tyrosine phenol group and serine and threonine hydroxyl groups. These functional groups (a) react with various functional groups (b) such as diazonium salts, acid amide, isocyanate, active alkyl halide groups and active ester groups. Thus, the functional group (a) is introduced into the reactive substance. Furthermore, the functional group (b) is introduced into the solid material surface. As a result, the reactive substance can be held on the solid material surface by a variety of methods.

On the other hand, the high-order structure of the reactive substance, particularly, a protein-containing reactive substance, is maintained through relatively weak bonds such as hydrogen, hydrophobic and ionic bonds. Therefore, such a high-order structure is fragile. Thus, it is desired that the immobilization of the reactive substance should be performed under mild conditions without performing high-temperature, strong acid and strong alkali treatments.

One method for performing immobilization reaction under mild conditions can utilize a bifunctional crosslinking agent that reacts with the functional groups of the solid material and the reactive substance. Examples of the bifunctional crosslinking agent include carbodiimide represented by the general formula R—N═C═N—R' and dialdehyde represented by the general formula CHO—R—CHO. Alternative examples thereof include diisocyanate represented by the general formula O═C═N—R—N═C═O. In these general formulas, R and R' are the same or different and each represents a substituted or unsubstituted alkyl, aryl, alkylaryl or arylalkyl group.

The treatment apparatus of the present invention may be used as an apparatus capable of stirring a solution, which includes the immobilized reactive substance. In such a case, the positional relationship between the electrodes and the immobilized reactive substance is important. Referring to, for example, the electrodes illustrated in FIG. 2, a solution flow occurs from the outer edge of the circular electrode toward the electrode in a radius direction thereof. On the other hand, a solution flow is relatively small from a region near the center of the circular electrode to a region in the facing direction. Therefore, the reaction substance can be immobilized in the container at a position from the outer edge of the circular electrode to the neighboring part thereof. The immobilization of the reactive substance at such a position produces large stirring effects. Thus, the reactive substance can be detected with high precision using the stirring effects. In actuality, the reactive substance is effectively immobilized at a position on the electrode or near the electrode, depending on the shape and size of the container used. These electrodes may be formed in a detection chip or may be formed on the apparatus side. Alternatively, the electrodes may be used as disposable electrodes or may be used repetitively.

(Biologically Relevant Substance)

In the present invention, the biologically relevant substance is added (introduced) into the solution for detection. This biologically relevant substance to be detected is not particularly limited and may be any of substances involved in in-vivo reaction. Specific examples thereof can include proteins, nucleic acids, microorganisms, cells and hormones. Further specific examples can include antigens and DNA. Examples of the specific reaction between the reactive substance and the biologically relevant substance can include specific binding reactions such as antigen-antibody reaction, DNA or RNA hybridization, an avidin-biotin bond and a sugar-boric acid bond.

Alternatively, examples of particularly clinicopathologically useful substances include the following substances: immunoglobulins such as IgG, IgM and IgE; plasma proteins such as complements, CRP, ferritin, $\alpha_1$ microglobulin and $\beta_2$ microglobulin, and antibodies thereof; tumor markers such as α-fetoprotein, carcinoembryonic antigen (CEA), prostatic acid phosphatase (PAP), CA19-9 and CA-125, and antibodies thereof; hormones such as luteinizing hormone (LH), follicle-stimulating hormone (FSH), human chorionic gonadotropin (hCG), estrogen and insulin, and antibodies thereof; viral infection-associated substances such as HBV-associated antigens (HBs, HBe and HBc), HIV and ATL, and antibodies thereof; bacteria such as *Corynebacterium diphtheriae, Clostridium botulinum, Mycoplasma* and *Treponema palli-*

*dum*, and antibodies thereof; protozoans such as *toxoplasma, trichomonas, leishmania, trypanosoma* and malarial parasites, and antibodies thereof; antiepileptic drugs such as phenyloin and phenobarbital; cardiovascular drugs such as quinidine and digoxin; antiasthmatic drugs such as theophylline; drugs such as antibiotics such as chloramphenicol and gentamycin, and antibodies thereof and other enzymes; and exotoxins such as streptolysin O, and antibodies thereof.

A substance that causes antigen-antibody reaction or the like with the reactive substance in the sample solution is appropriately selected for use.

(Electrode)

The placement and shape of electrodes play a very important role in causing the desired flow in a solution in the container. The shape of electrodes may be, in additions to plate, square and circular forms listed herein, various forms such as dot, linear, comb-like, star-shaped, multi-ring, rod-like, cylindrical, triangular pyramid-shaped, needle-like and hole-shaped forms or a population of these forms. Alternatively, the electrodes may be a combination of these forms or may be placed in an array form. This shape of electrodes as well as the placement of electrodes may be selected appropriately according to the container used and the desired flow. Alternatively, the electrodes may have a planar surface or may have a curved surface. The number of each of the electrodes (cathode and anode) may be one or more. The numbers, sizes and shapes of the cathode and the anode may be the same or different. For example, the treatment apparatus may include a single electrode as one of the cathode and the anode. In such a case, this electrode can serve as a large electrode constituting the whole part of one inner wall of the container. Alternatively, the treatment apparatus may include two or more electrodes as one of the cathode and the anode, these electrodes can serve as a plurality of small electrodes provided in one inner wall of the container.

The electrodes of the present invention include one or more working electrode(s) and one or more counter electrode(s) and may optionally include a reference electrode. The use of the reference electrode can measure the electric potentials of the working and counter electrodes, with the electric potential of the reference electrode as a reference electric potential.

An electrode material used has conductivity and sufficient rigidity and has sufficient electrochemical stability under conditions for use of the electrodes.

The present invention requires the electrode reaction of the oxidation-reduction substances for causing a solution flow. Therefore, a suitable material used for the electrodes has a low overvoltage in the reaction with the oxidation-reduction substances in the solution, that is, has a high catalytic ability for the reaction with the oxidation-reduction substances in the solution.

Examples of such an electrode material can include: metals such as gold and platinum; conductive polymers such as polypyrrole and polythiophene; and metal oxides containing In, Sn or Zn. Furthermore, examples of a material constituting a conductive member can include carbon materials such as graphite, carbon black, carbon nanotube, carbon nanohorn and fullerene compounds. Alternatively, a composite material of two or more of these materials, a polymer material containing these electrode materials dispersed as conductive fillers, or a conductive polymer material such as polypyrrole may be used. Alternatively, the electrode material may be a composite material containing a conductive material layer provided on a base surface.

An appropriate catalyst may be added onto such a material. Examples of this catalyst include metals or fine particles thereof, metal oxides or fine particles thereof, carbon materials and enzymes. Specific examples thereof include fine particles of gold, platinum, silver, palladium or rhodium, fine particles of iridium oxide or an indium tin oxide (ITO), graphite, carbon black, carbon nanotube, carbon nanohorn, fullerene compounds, glucose oxidase, glucose dehydrogenase, lactate oxidase, alcohol dehydrogenase, peroxidase, laccase and bilirubin oxidase. Alternatively, this electrode may also be used as a concentration detection site for a substrate contained in the solution.

A reference electrode may be used, as described above. In such a case, the reference electrode may be any of electrodes that have stability and can conveniently specify the electric potential of the electrode to be measured. Examples thereof include a silver/silver chloride electrode. This electrode may optionally be provided with a layer for preventing the adsorption and deposition of the reaction substance. Examples of this adsorption/deposition-preventing layer include polymer compounds and low-molecular-weight compounds. More specific examples thereof include casein, skimmed milk, bovine serum albumin, polymer compounds (including fluorine-containing polymers), dialysis membranes, thiol compounds and silane compounds.

Examples of effects of an electrode size include the following items: (1) changes in electric current density and the control of a flow of the oxidation-reduction substances; and (2) a response to solution resistance.

Hereinafter, these items will be described with reference to illustrations.

Figure 4:
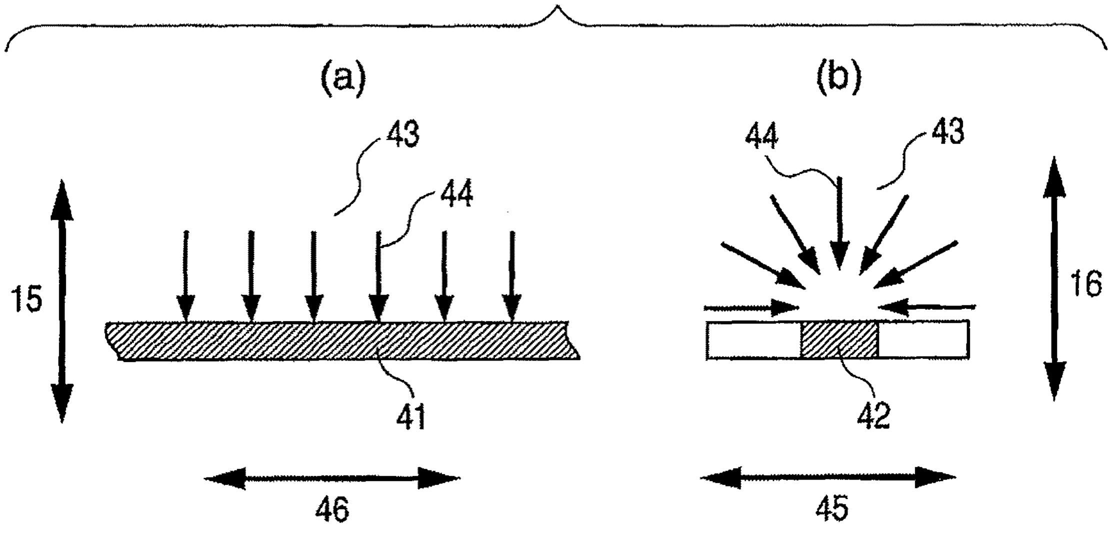
FIG. 4 is an illustrative diagram depicting the relationship between an electrode size and a solution flow.

(1) Changes in electric current density and control of flow of oxidation-reduction substances FIG. 4 illustrates schematic diagrams of two plate electrodes differing in size. The left diagram illustrates a large-size electrode 41, while the right diagram illustrates a small-size electrode 42. The upper surfaces of both of these electrodes are brought into contact with a solution 43. In the diagrams, the arrows indicate a flow 44 of oxidation-reduction substances to be oxidized or reduced at the electrode. To a sufficiently large electrode, the oxidation-reduction substances are supplied from a direction perpendicular to the electrode, as illustrated in the left diagram of FIG. 4. On the other hand, to an electrode having a sufficiently small area, the oxidation-reduction substances are supplied from various directions, as illustrated in the right diagram of FIG. 4. Therefore, substrate (here, the oxidation-reduction substance) diffusion-limited current density (is rendered high. Therefore, the electric current density can be improved by decreasing an electrode area, in a system in which the electric current value of oxidation-reduction substances in the solution is limited by the diffusion process of the oxidation-reduction substances. This effect is produced by decreasing an electron size, regardless of a scale. However, this effect is significantly produced by using, for example, an electrode on the micrometer order.

Figure 5:
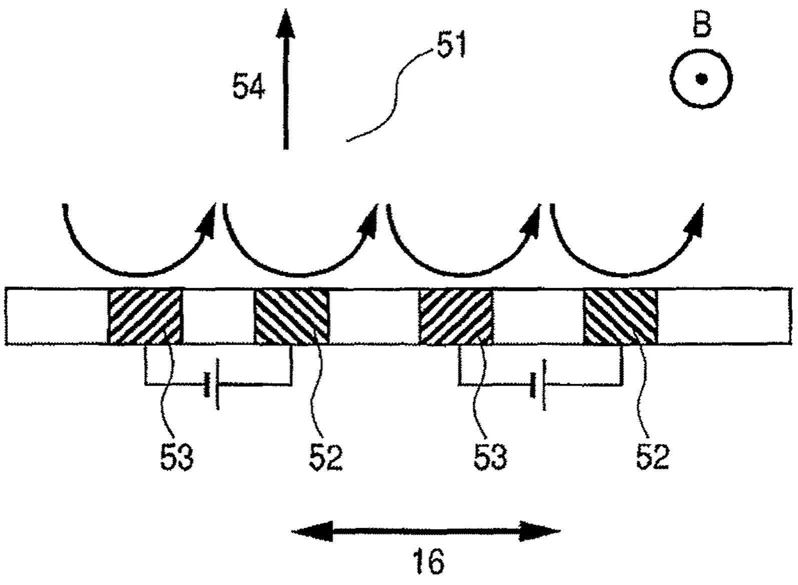
FIG. 5 is an illustrative diagram depicting one example of placement of electrodes using a redox cycle according to the present invention.

Furthermore, small electrodes may be used in combination and placed in proximity to each other. For example, disc electrodes arranged as illustrated in FIG. 2 or comb-like electrodes may be used. In such a case, a positive electric potential capable of oxidizing reduced forms of the oxidation-reduction substances is applied to one of the electrodes placed in proximity to each other. Moreover, a negative electric potential capable of reducing oxidized forms of the oxidation-reduction substances is applied to the other electrode. As a result, a mechanism called a redox cycle as illustrated in FIG. 5 amplifies an electric current, as previously known. This is due to an event in which oxidized forms produced by the oxidation of the reduced forms of the oxidation-reduction substances at one of the electrodes (i.e., at an electrode 52) are reduced at an electrode 53 immediately adjacent to the electrode 52 (vice versa) in the state of contact between a oxidation-reduction substance-containing solution 51 and the upper surface of the electrode. Alternatively, to a planar electrode having a sufficiently small area, the oxidation-reduction substances are supplied from various directions, as illustrated in the right diagram of FIG. 4. Therefore, a flow of the oxidation-reduction substance has components in a direction horizontal to the electrode. Specifically, the electrode size can be controlled so as to control the flow of the oxidation-reduction substances.

Examples of a system for which this control is effective can include the relationship between the placement of electrodes and a magnetic field illustrated in FIG. 2. In this case, components of a flow of the oxidation-reduction substances perpendicular to the electrode do not generate force that causes a solution flow. By contrast, components of a flow of the oxidation-reduction substances horizontal to the electrode cause a solution flow. Therefore, the electrode size can be decreased so as to generate a force that causes a solution flow, that is, achieve, in the solution, a flow of the oxidation-reduction substances having components horizontal to the electrode. Alternatively, the electric current density can be increased so as to increase Lorentz force that eventually acts on the solution.

(2) Response to Solution Resistance

For allowing electrode reaction to proceed, it is desired that a solution for dissolving the oxidation-reduction substances should have high conductivity, as described later. However, the ionic strength of the solution cannot be set high under some circumstances, for example, for the purpose of stably maintaining the reactive substance. In this case, small electrodes can be used in combination and placed in proximity to each other, as illustrated in FIG. 5, so as to reduce the influence of solution resistance.

(Oxidation-Reduction Substance)

The interaction between current cased by reaction of oxidation-reduction substances contained in the solution and magnetic field causes solution flow. The oxidation-reduction substances are oxidized or reduced at the electrode through the application of a certain electric potential or voltage. As a result, an electrolytic current is generated. Force proportional to the electrolytic current density can be generated by the interaction between this electrolytic current and an outside magnetic field so as to cause a solution flow. The oxidation-reduction substances, unlike conventional magnetic substances dispersed in a solution, are dissolved in a solution. Therefore, the oxidation-reduction substances have the advantage that the aggregation or uneven distribution of magnetic substances hardly has to be considered.

Examples of properties that may be necessary for the oxidation-reduction substances include the following properties: (1) high solubility in the solution; (2) high diffusion coefficient in the solution; (3) fast electron transfer at the electrode; (4) high electrochemical stability; and (5) little inhibition of the interaction of the biologically relevant substance or stable inhibitory effects thereon.

These properties are required for reasons described below.

(1) The high solubility in the solution can eliminate a limited current attributed to the diffusion of the oxidation-reduction substances to the electrode. This can generate a high electrolytic current and increase force that causes a solution flow. Moreover, this high solubility can prevent the deposition of the oxidation-reduction substances in a system resulting from factors such as temperature difference so as to stably achieve the detection of a biologically relevant substance with high precision.

(2) The high diffusion coefficient in the solution can eliminate a limited current attributed to the diffusion of the oxidation-reduction substances to the electrode. This can generate a high electrolytic current and increase force that causes a solution flow. This can also reduce the amount of the oxidation-reduction substances used.

(3) The fast electron transfer at the electrode can eliminate a limited current attributed to a charge transfer process in the electrode. This can also generate a high electrolytic current and increase force that causes a solution flow. This can further promote reaction at a low overvoltage and reduce consumed electric energy.

(4) The high electrochemical stability can prevent a decrease in the concentration of the oxidation-reduction substances attributed to their structural change and can prevent the deposition of the oxidation-reduction substances onto the electrode so as to stably generate a high electrolytic current. This can also generate highly stable force that causes a solution flow.

(5) The oxidation-reduction substances are dissolved for use in the solution targeted for causing a flow. The oxidation-reduction substances may be used in a solution also containing the biologically relevant substance and the reactive substance. Therefore, the oxidation-reduction substances should not inhibit the reaction between the biologically relevant substance and the reactive substance. The use of such oxidation-reduction substances can stably detect the desired biologically relevant substance with high precision. Alternatively, the oxidation-reduction substances may promote the reaction between the biologically relevant substance and the reactive substance.

Examples of the oxidation-reduction substances include metal complexes, quinones and heterocyclic compound. Further specific examples thereof include hexacyanoferrate, ferrocene derivatives, quinones and viologen derivatives.

The oxidation-reduction substances may be present in at least one of oxidized and reduced forms in the solution and can be present in both of the forms. Alternatively, only one of the oxidized and reduced forms may be contained initially in the solution, and its partner may be produced by electrode reaction.

(Solvent)

Examples of properties necessary for a solvent for dissolving the oxidation-reduction substances include the following properties: (1) high solubility at which the oxidation-reduction substances can be dissolved; (2) stability with which the biologically relevant substance and the reactive substance can be dissolved and dispersed; and (3) high conductivity.

These properties are required for reasons described below.

(1) The high solubility is required for the same reason as in the property (1) that may be necessary for the oxidation-reduction substances.

(2) The oxidation-reduction substances may be used in the solution also containing the biologically relevant substance and the reactive substance, as described above. In such a case, the stability with which the biologically relevant substance and the reactive substance can be dissolved and dispersed can stably maintain these substances.

(3) The promotion of electrochemical reaction in the proximity to the electrode is necessary for generating a high electrolytic current. This promotion requires forming a large electric potential gradient in the proximity of the electrode. This formation requires the high conductivity of an electrolytic solution.

Examples of this solvent include a variety of aqueous buffer solutions with a salt concentration of approximately 0.01 M or higher and 1 M or lower. Alternatively, these aqueous buffer solutions may be supplemented with an organic solvent, for example, glycerol, for use.

(Magnetic Field Application Unit)

The magnetic field application unit of the present invention is configured to be capable of applying, for example, a magnetic field containing components parallel with or perpendicular to the facing direction of the electrodes. Specifically, in the treatment apparatus of the present invention, a predetermined voltage or electric potential is applied so as to cause a flow of the oxidation-reduction substances in a predetermined direction to the electrode. A magnetic field is applied according to this direction of the electrolytic current. As a result, Lorentz force can eventually act on the solution in a predetermined direction by the interaction between the electrolytic current and the magnetic field so as to cause a solution flow.

The magnetic field applied from outside generates force that causes a solution flow by the interaction thereof with the electrolytic current generated by electrode reaction. This force is increased in proportion to a magnetic flux density. Therefore, for causing an effective solution movement, it is desired that the magnetic flux density of the present treatment apparatus should be large sufficiently, for example, 10 mT or more.

The treatment apparatus of the present invention can have a magnet as the magnetic field application unit. This magnet may be a single magnet or may be a plurality of magnets. Moreover, the magnet may be a permanent magnet or may be an electromagnet. Examples of advantages of use of the electromagnet include the following advantages: (1) the polarity of an electric current applied to the magnet can be changed so as to control the direction of a movement caused in the solution; and (2) the magnitude of an electric current applied to the magnet can be controlled so as to control the magnitude of a movement caused in the solution.

Alternatively, examples of advantages of use of the permanent magnet include the following advantage.

(1) the permanent magnet does not require an electric energy for generating magnetic force, leading to reduction in power requirements.

For the electromagnet used, for example, an electric current applied to the magnet may be controlled. Alternatively, for the permanent magnet used, for example, the magnet may be moved, or a substance that reduces the magnetic flux density may be inserted thereinto. As a result, the magnetic flux density can be controlled in the corresponding region. These control mechanisms may be achieved by sequence or feedback control based on computerized control. This mechanism may be housed in a case separated from the magnet portion or the container.

(Electric Potential or Voltage Application Unit)

The electric potential or voltage applied to the electrodes generates an electric current by the oxidation or reduction of the oxidation-reduction substances present in the solution at the electrodes. This electric current generates force that causes a solution flow by the interaction thereof with a magnetic field. This force is increased in proportion to an electric current value. Therefore, for causing an effective solution movement, a sufficient electric current value is required. Therefore, the electrical potential or voltage applied to the electrodes must be applied at a value necessary for the sufficient electric current value.

For example, electrode reaction attributed to the application of the electric potential or voltage may be the reduction reaction of the oxidation-reduction substances. In such a case, the electric potential applied to the electrode can be more negative than the oxidation-reduction potential of the oxidation-reduction substances. Alternatively, electrode reaction attributed to the application of the electric potential or voltage may be the oxidation reaction of the oxidation-reduction substances. In such a case, the electric potential applied to the electrode can be more positive than the oxidation-reduction potential of the oxidation-reduction substances. On the other hand, the application of an excessively large voltage or the application of an excessively negative or positive electric potential sometimes induce unfavorable reaction such as solvent decomposition, the irreversible reaction of the oxidation-reduction substances and the deposition of other substances contained in the solution. Therefore it is important to set the applied electric potential or voltage to a proper value according to the composition of the solution.

In a simple way, the application of a stationary voltage is used as an application pattern of the applied electric potential or voltage. Additionally, a variety of patterns can be used as required. Examples thereof include stationary waves, stepped waves, sine waves and pulse waves. However, the driving force of the method for causing a solution flow according to the present invention is brought about by Lorentz force generated by the interaction between a faradaic current (and a substrate flow caused thereby) generated by the oxidation-reduction reaction of the oxidation-reduction substances at the electrode and a magnetic field. An alternating-current potential or voltage that spans the electric potentials for the oxidation and reduction of the oxidation-reduction substances may be applied. Under this circumstance, the period of waveforms of the applied electric potential or voltage may be shorter than the reaction rate of the oxidation-reduction substances at the electrode. In such a case, the reaction of the oxidation-reduction substances does not occur at the electrode. Therefore, this application probably causes almost no solution flow. Moreover, a certain interval is probably required from when an electric current attributed to the reaction of the oxidation-reduction substances is generated to when a solution movement is caused. The application of an alternating-current potential or voltage that spans the electric potentials for the oxidation and reduction of the oxidation-reduction substances in a time range much shorter than this interval is inappropriate from the viewpoint of causing a solution flow. In this case, the significance of this application is largely reduced. This applied electric potential or voltage may be controlled by sequence or feedback control based on computerized control. This mechanism may be housed in a case separated from the magnet portion or the container.

(Detection Method and Whatnot)

In the present invention, a reaction product from the reactive substance reacted with the biologically relevant substance can be detected by a predetermined detection method. Each of conventional methods known in the art can be utilized as this detection method. Examples thereof include enzyme electrodes, oxygen electrodes, hydrogen peroxide electrodes, field-effect transistors, ion electrodes, luminescent detection, surface plasmon resonance, localized surface plasmon resonance, quartz oscillators and calorimetry.

The container of the present invention, the thin tube of the present invention or their accessories may have additional mechanisms, for example, a temperature control mechanism, additional optical detection mechanisms, a sample injection mechanism, a valve mechanism and a washing mechanism, according to the intended use.

As described above, Lorentz force generated by the interaction between an electrolytic current generated by the electrochemical reaction of oxidation-reduction substances dissolved in a solution and an outside magnetic field is utilized in the present invention. As a result, a solution movement can be caused without the use of pumps, stirrers and magnetic substances dispersed in a solution. Effects produced by the present invention are listed below.

(1) Oxidation-reduction substances for causing a solution flow are dissolved in a solution. Therefore, unlike magnetic beads or the like, problems such as aggregation and segregation do not appear.

(2) The ON/OFF, inversion and strength adjustment of a solution flow caused by MHD effects can be achieved easily by the control of an applied electric potential or voltage or an applied magnetic field.

(3) a flow in a desired direction can selectively be caused in a predetermined region in a solution according to the placement, shape and size of electrodes and the application pattern of an electric potential or voltage.

(4) The oxidation-reduction substances for causing a solution flow are molecules. Therefore, unlike magnetic beads or the like, the oxidation-reduction substances are not likely to strip off, for example, a material for detecting a biologically relevant substance, a nonspecific interaction-preventing layer and a protective layer.

As a result, the treatment apparatus can reduce the reaction time of the biologically relevant substance and set a concentration limit of detection to a lower value.

EXAMPLES

Hereinafter, the present invention will be described in more detail with reference to Examples. However, a method of the present invention is not limited only to these Examples. Prior to Examples, Preparation Example of a Material Used in Examples Will be described.

Preparation Example 1 Preparation of Osmium Complex Polymer

Hereinafter, a method for synthesizing a complex polymer represented by the formula (1) below will be described. This complex polymer corresponds to a solid material for immobilizing a reactive substance thereon and transfers, to electrodes, electrons generated by the reaction of an enzyme used as a label.

(Chemical Formula 1)

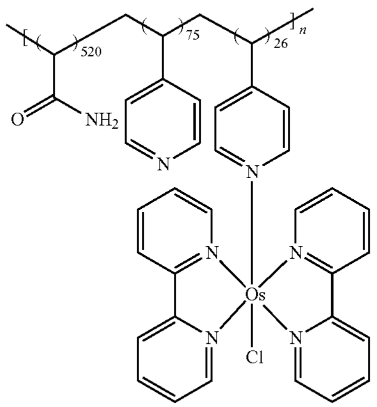

To a 100-mL round-bottomed flask connected with a reflux tube, 20 mL of ethylene glycol, 0.08 g of $(NH_4)_2[OsCl_6]$ and 0.32 g of 2,2'-bipyridine were added and stirred with a stirrer. Simultaneously with this procedure, the mixture was irradiated at 300 W for 20 minutes with a microwave synthesizer (Milestone microsynth) under a nitrogen stream. Next, this solution was allowed to cool to room temperature. Then, 25 mL of water containing 0.4 g of $Na_2S_2O_4$ dissolved therein was added thereto.

After 1-hour stirring at room temperature, the produced dark purple precipitate was recovered by filtration and washed with water to remove excessive salts. The resulting precipitate was washed with diethyl ether to remove unreacted ligands. The precipitate was dried by heating to 60° C. under reduced pressure to obtain $Os(2,2'\text{-bipyridine})_2Cl_2$.

To a 100-mL three-neck flask equipped with a thermometer and a reflux tube, 15 mL of water, 15 mL of acetone, 2.3 g of acrylamide, 0.50 mL of 4-vinylpyridine and 0.060 mL of N,N,N',N'-tetramethylethylenediamine were added. Next, 0.055 g of ammonium persulfate was further added thereto under a nitrogen stream. The mixture was heated at 40° C. in a water bath for 13 hours. Then, the container was air-cooled. The produced viscous liquid was added dropwise to 800 mL of acetone under vigorous stirring and precipitated. The precipitate was collected by centrifugation. Next, water was added in the minimum amount capable of dissolving this precipitate to dissolve the precipitate. This aqueous solution was further added dropwise to 800 mL of acetone under vigorous stirring and precipitated. The precipitate was collected again by centrifugation and dried by heating to 60° C. under reduced pressure to obtain a polyacrylamide-polyvinylpyridine 5.2/1 copolymer (unit ratio). The molecule production and the unit ratio were measured by $^1$HNMR measurement ($D_2O$).

To a 100-mL round-bottomed flask connected with a reflux tube, 15 mL of ethylene glycol, 0.11 g of the $Os(2,2'\text{-bipyridine})_2Cl_2$ thus prepared and 0.12 g of the polyacrylamide-polyvinylpyridine copolymer thus prepared were added and stirred with a stirrer. Next, the mixture was irradiated at 400 W for 20 minutes with a microwave synthesizer under a nitrogen stream. The solution was allowed to cool to room temperature. Then, the solution supplemented with 10 mL of ethanol was added dropwise to 500 mL of a diethyl ether solution under vigorous stirring. Next, 10 mL of ethanol was further added to the resulting viscous precipitate. This solution was added dropwise again to 500 mL of a diethyl ether solution under vigorous stirring. The viscous precipitate thus obtained was dried by heating t 60° C. under reduced pressure to obtain the desired complex polymer represented by the formula (1).

Example 1

Figure 6:
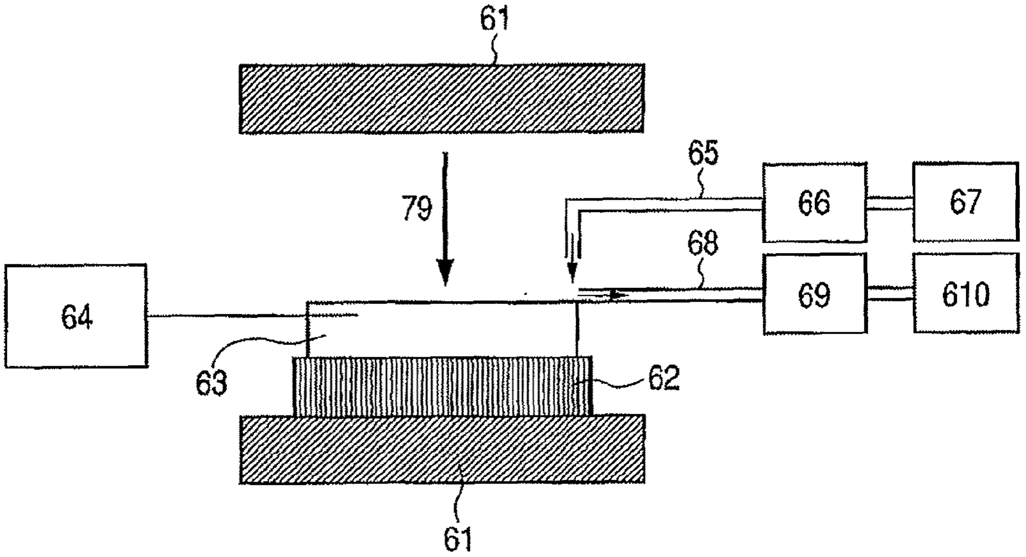
FIG. 6 is a schematic diagram depicting one embodiment of a treatment apparatus of the present invention.

A treatment apparatus of this Example includes a plurality of circular planar electrodes and a single large planar electrode and achieves DNA detection using an enzyme electrode system. FIG. 6 depicts this treatment apparatus. This drawing illustrates one embodiment of a treatment apparatus for stirring a reaction solution in a container by Lorentz force generated by the interaction between an electric current and a magnetic field while performing a reaction step for detecting a biologically relevant substance. This FIG. 6 is a conceptual diagram of the cross section of this apparatus in a perpendicular direction.

This apparatus includes a magnet 61, a temperature controller 62, a container 63 for retaining a solution, a power supply 64 (e.g., a potentiostat), an inlet tube 65 for introducing a solution and a sample, a pump 66 and its reservoir 67, an outlet tube 68 for discharging the sample and a pump 69 and its reservoir 610.

Figure 7:
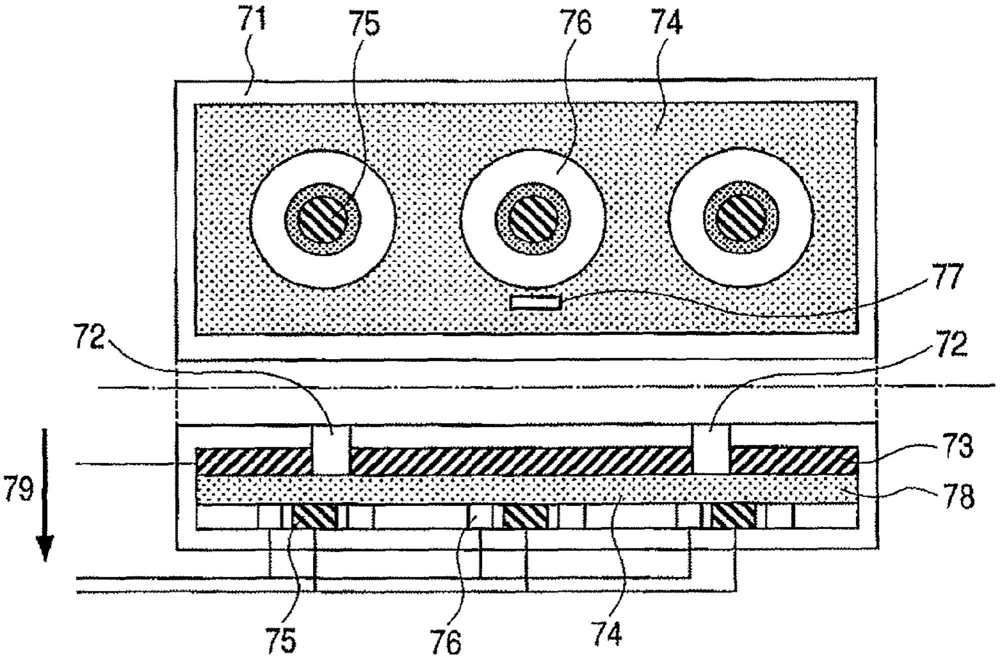
FIG. 7 is a schematic diagram depicting one embodiment of a treatment apparatus of the present invention.

This container 63 for retaining a solution is illustrated in detail in FIG. 7. The upper diagram (bottom view) of FIG. 7 illustrates the shape of the circular electrodes in the inner bottom surface of the container. The lower diagram of FIG. 7 illustrates a cross-sectional view of the container. The container is surrounded by an outer frame 71. This outer frame is made of, for example, a polyimide resin and provided in the upper surface thereof with an opening 72 for injecting or discharging a sample, an air, a washing solution and so on. The outer frame has a hollow structure. A single planar electrode 73 constituting a first inner wall 78 is formed on the inner upper surface of the outer frame. A hollow space 74 is filled with a sample, an air, a washing solution and so on. The inner bottom surface of this hollow outer frame is provided with a plurality of circular electrodes 75 facing the planar electrode 73. Ring electrodes 76 surrounding the electrodes 75 are formed so as to provide insulation between the electrodes 76 and the electrodes 75. These electrodes are connected to a potentiostat as an outside power supply via leads.

These electrodes are made of, for example, screen-printed carbon electrodes. In this context, the prevention of reduction in the magnetic flux density of the electrodes requires limiting the designed position of the electrodes. For the purpose of eliminating this requirement, a material with low relative permeability can be used as the electrodes. A reference electrode 77 made of, for example, a commercially available silver paste for a reference electrode is further formed in the inner bottom surface by screen printing. The Os complex polymer prepared in Preparation Example 1 and a 5'-amine-terminated oligonucleotide for capture are immobilized in advance through electrodeposition in the electrodes 76.

An approach for the immobilization through electrodeposition was conducted according to the following procedures: a phosphate buffer solution containing 18% by mass of 1 $mg \cdot mL^{-1}$ Os complex polymer was added dropwise onto the electrodes 76. To the electrodes 76, −1.4 V vs. Ag/AgCl was applied for 20 seconds with the potentiostat. Then, the electrodes were washed with deionized water so as to immobilize thereon the Os complex polymer through electrodeposition. After this immobilization through electrodeposition, for example, a phosphate buffered saline (PBS) containing 2 μM 5'-amine-terminated oligonucleotide for capture (reactive substance; DNA) having the sequence SEQ ID NO:1 was added dropwise onto the electrodes 76. To the electrodes 76, −1.4 V vs. Ag/AgCl was applied for 20 seconds with the potentiostat. Then, the electrodes were washed with deionized water.

The temperature controller 62 was set to, for example, 53° C. For example, a hybridization buffer solution containing a target oligonucleotide (biologically relevant substance) having the sequence SEQ ID NO:2, 5 mM $K_3[Fe(CN)_6]$ and 5 mM $K_4[Fe(CN)_6]$ was introduced from the reservoir 67 through the inlet tube 65 and the opening 72 into the hollow space 74. In this context, the electrodes 75 were used as working electrodes (anodes); the electrode 73 was used as a counter electrode (cathode); and the electrode 77 was used as a reference electrode. The electric potential of the electrodes 75 was set to 0.5 V vs. Ag/AgCl. An electric current was applied to the electromagnet so as to apply a magnetic field in a downward direction 79 in FIG. 6. Examples of the magnetic flux density in this case include 1 T. After 10-minute reaction, the reaction solution was kept at room temperature for 10 minutes. The application of the electric potential and the magnetic filed was terminated. The inner space of the container was washed with a hybridization buffer solution.

Then, a hybridization buffer solution containing 50 nM oligonucleotide for detection, for example, horseradish peroxidase (HRP)-modified oligonucleotide (label for the biologically relevant substance) having the sequence SEQ ID NO:3, 5 mM $K_3[Fe(CN)_6]$ and 5 mM $K_4[Fe(CN)_6]$ was introduced into the hollow space. Then, the same electric potential and magnetic field as above were applied thereto. After 10-minute reaction at 37° C., the reaction solution was kept at room temperature for 10 minutes. The application of the electric potential and the magnetic filed was terminated. The inner space of the container was washed with a hybridization buffer solution until the electric current of the cyano complex of iron was undetectable.

Then, PBS containing 0.2 mM $H_2O_2$ was added to the container. The electric potential of the electrodes 76 was set to 0.2 V vs. Ag/AgCl. The stationary electric current was observed. On the other hand, the same procedures as above except for the application of a magnetic field were conducted as a control experiment. This control experiment was used as Comparative Example 1.

In this treatment apparatus, a flow of the oxidation-reduction substances occurs in the proximity of the electrodes 75 in a direction perpendicular to the facing direction of the electrodes. An electrolytic current attributed to the flow in this direction generates Lorentz force by the interaction thereof with a magnetic field (downward direction in FIG. 7; direction parallel with the facing direction). Then, this Lorentz force causes a solution flow. The solution is stirred by this flow so as to promote the reaction (hybridization) between the reactive substance (oligonucleotide) and the biologically relevant substance (oligonucleotide).

In this Example, the oligonucleotide to be detected is hybridized with the oligonucleotide for capture as a reactive substance. The HRP-modified oligonucleotide as a label is further hybridized with the oligonucleotide to be detected. As a result, the enzyme reaction of HRP catalyzes the oxidation of hydrogen peroxide, which then generates an electron. This electron is collected by the electrode through the osmium complex so as to generate a stationary electric current.

Figure 8:
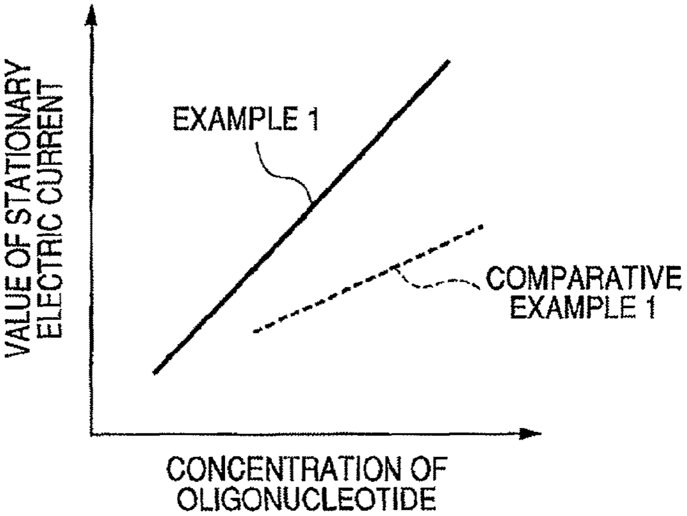
FIG. 8 is a conceptual diagram depicting detection results of Example 1 and Comparative Example 1.

The observation results were plotted with the value of the observed stationary electric current as an ordinate against the concentration of the added oligonucleotide as an abscissa. The observation results thus plotted exhibited a tendency illustrated in FIG. 8. Specifically, Example 1 using a magnetic field applied for hybridization resulted in a large value of the stationary electric current observed at the same concentration of the added oligonucleotide, as compared with Comparative Example 1 using no applied magnetic field. Moreover, Example 1 achieved detection even at a low concentration of the oligonucleotide, as compared with Comparative Example 1.

This is probably because the stirring of a solution by MHD effects produced by the interaction between the magnetic field applied during hybridization and the electrolytic current promotes the hybridization reaction.

Example 2

Figure 9:
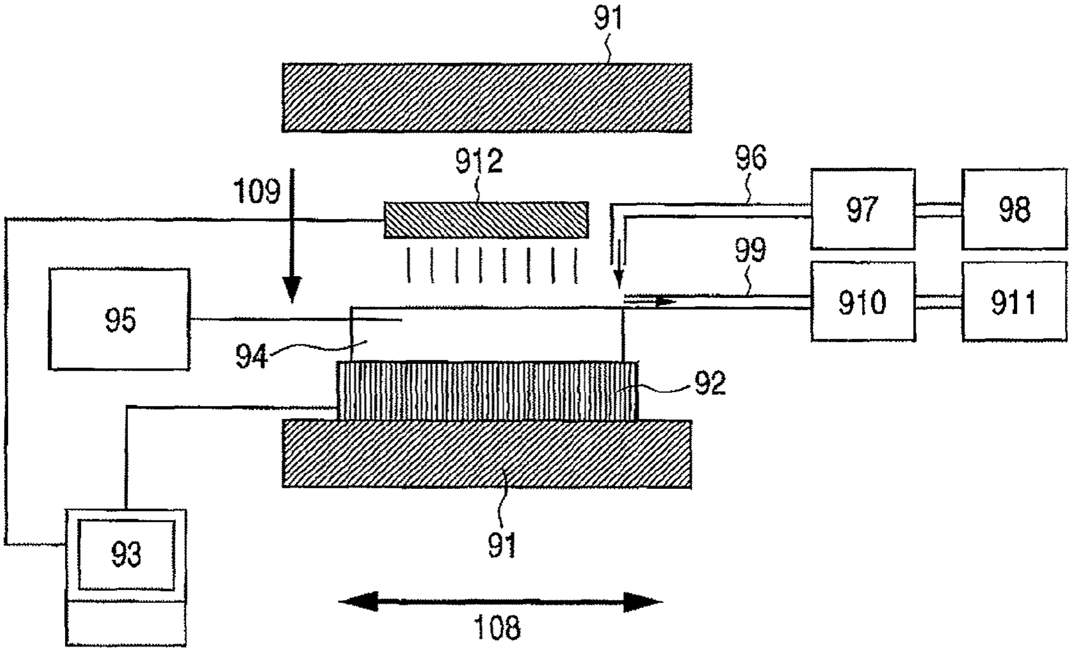
FIG. 9 is a schematic diagram depicting one embodiment of a treatment apparatus of the present invention.

A treatment apparatus of this Example includes a plurality of circular electrodes provided as a plurality of pairs of cathodes and anodes in one inner wall of a container and stirrers a solution by a redox cycle so as to achieve detection based on the localized surface plasmon of an antigen-antibody reaction product. FIG. 9 depicts this treatment apparatus. This drawing illustrates one embodiment of a treatment apparatus for stirring a reaction solution in a container by Lorentz force generated by the interaction between an electric current and a magnetic field while performing a reaction step. This FIG. 9 is a conceptual diagram of the cross section of this apparatus in a perpendicular direction.

This apparatus includes a magnet 91, a photodiode array 92, an apparatus 93 for performing the operation and analysis of the photodiode array and the operation and analysis of a monochromatic light source, a container 94 for retaining a solution and a power supply 95 (e.g., a potentiostat). The apparatus also includes an inlet tube 96 for introducing a solution and a sample, a pump 97 and its reservoir 98, an outlet tube 99 for discharging the sample, a pump 910 and its reservoir 911 and a monochromatic light source 912.

Figure 10:
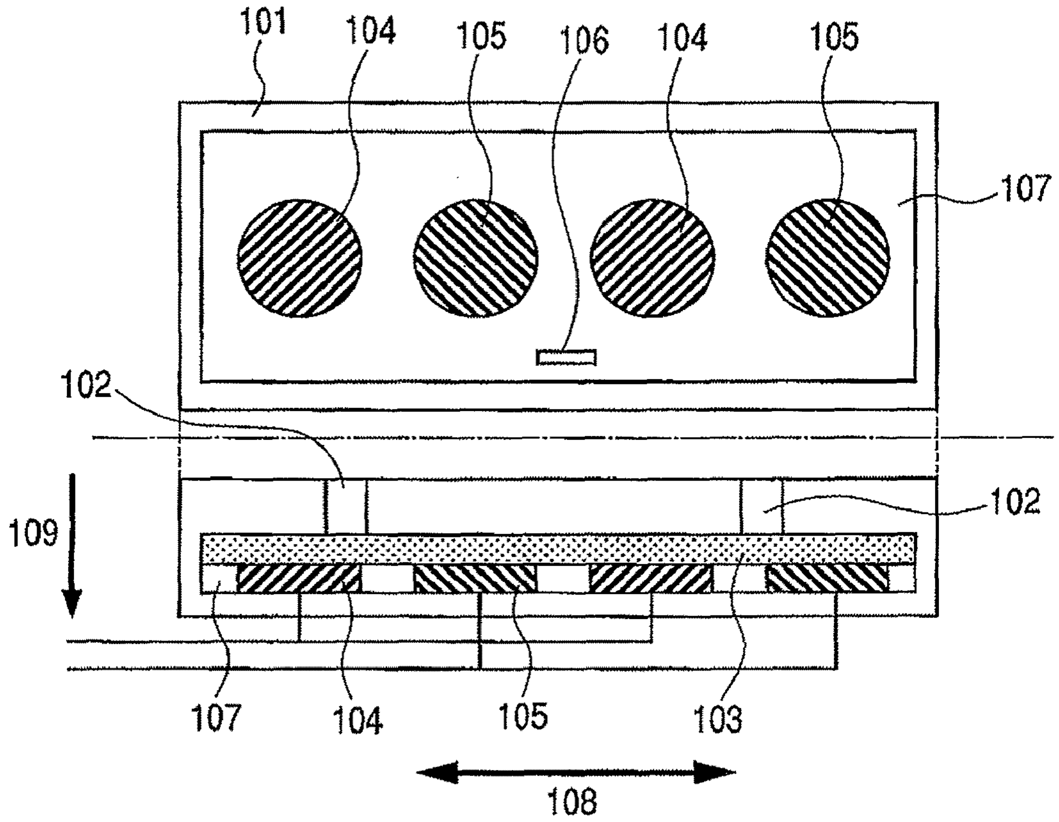
FIG. 10 is a schematic diagram depicting one embodiment of a treatment apparatus of the present invention.

FIG. 10 illustrates a detail diagram of this container 94 for retaining a solution used here. The upper diagram (bottom view) of FIG. 10 illustrates the shape of the circular electrodes in the inner bottom surface of the container. The lower diagram of FIG. 10 illustrates a cross-sectional view of the container. The container is surrounded by an outer frame 101. This outer frame is made of, for example, a polystyrene resin and is transparent. The outer frame is provided in the upper surface thereof with an opening 102 for injecting or discharging a sample, an air, a washing solution and so on. The outer frame has a hollow structure. A hollow space 103 is filled with a sample, an air, a washing solution and so on. Four circular electrodes are placed in the inner bottom surface of this hollow outer frame. Adjacent two electrodes of these four electrodes are used as a set (anode and cathode). These electrodes in each set are electrically connected to each other and face each other in a facing direction 108. These electrodes are connected to a potentiostat as an outside power supply via leads. These electrodes are made of, for example, screen-printed carbon electrodes. A reference electrode 106 made of, for example, a commercially available silver paste for a reference electrode is further formed in the inner bottom surface by screen printing.

In an electrode-surrounding region 107, gold fine particles (solid material also serving as a causative substance of plasmon absorption) are immobilized via, for example, a commercially available surface-aminated polystyrene base. A commercially available antibody (e.g., anti-rabbit IgG: reactive substance) for capturing a biologically relevant substance is immobilized in advance in these gold fine particles.

For example, a PBS solution of target rabbit IgG (biologically relevant substance) containing 5 mM $K_3[Fe(CN)_6]$ and 5 mM $K_4[Fe(CN)_6]$ was introduced at room temperature from the reservoir 98 through the inlet tube 96 and the opening 102 into the hollow space 103. The electric potential of the electrodes 104 was set to 0.0 V vs. Ag/AgCl, while the electric potential of the electrodes 105 was set to 0.5 V vs. Ag/AgCl. An electric current was applied to the electromagnet so as to apply a magnetic field in a downward direction 109 in FIG. 9. The polarity of this electromagnet is reversed every 5 minutes. Examples of the magnetic flux density in this case include 1 T. After 30-minute reaction, the application of the electric potential and the magnetic filed was terminated. The inner space of the container was washed with PBS until the influence of the cyano complex of iron was undetectable.

In this treatment apparatus, a flow of the oxidation-reduction substances occurs between the electrodes 104 and 105 in the facing direction 108 of the electrodes. An electrolytic current attributed to the flow in this direction generates Lorentz force by the interaction thereof with a magnetic field applied in a direction perpendicular to the facing direction 108 (downward direction 109 in FIG. 9). Then, this Lorentz force causes a solution flow rotating around the electrodes. The solution is stirred by this flow.

Then, the wavelength of the monochromatic light source was scanned. Absorption spectra were determined from a photodiode response. The shifted peak wavelength of plasmon absorption of the gold fine particles was observed. On the other hand, the same procedures as above except for the application of a magnetic field were conducted as a control experiment. This control experiment was used as Comparative Example 2.

Figure 11:
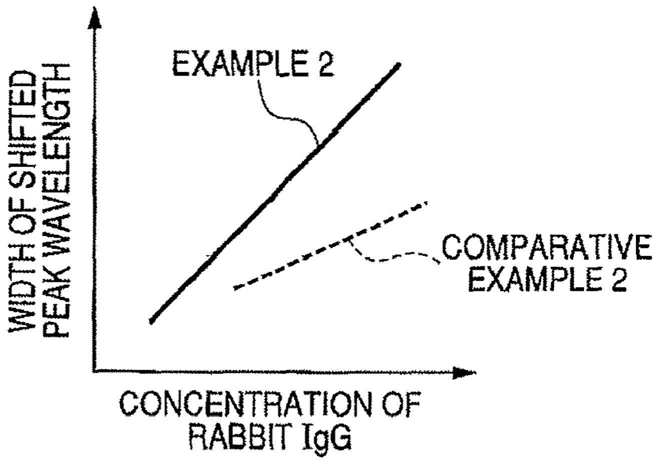
FIG. 11 is a conceptual diagram depicting detection results of Example 2 and Comparative Example 2.

The observation results were plotted with the width of the observed shifted peak wavelength as an ordinate against the concentration of the added rabbit IgG as an abscissa. The observation results thus plotted exhibited a tendency illustrated in FIG. 11. Specifically, Example 2 using a magnetic field applied for antigen-antibody reaction resulted in a large width of the shifted peak wavelength observed at the same concentration of the added antigen, as compared with Comparative Example 2 using no applied magnetic field. Moreover, Example 1 achieved detection even at a low concentration of the antigen, as compared with Comparative Example 1.

In this Example, the rabbit IgG as a biologically relevant substance to be detected is reacted through antigen-antibody reaction with the ant-rabbit IgG for capture as a reactive substance. As a result, a dielectric constant in the neighborhood of the gold fine particles is changed. Therefore, the plasmon absorption of the gold fine particles is changed.

This is probably due to a mechanism called a redox cycle, which amplifies an electric current between adjacent electrodes during the application of an electric potential. This electric current produces larger MHD effects by the interaction thereof with a magnetic field. The solution is stirred by the MHD effects so as to promote antigen-antibody reaction.

Example 3

Figure 12:
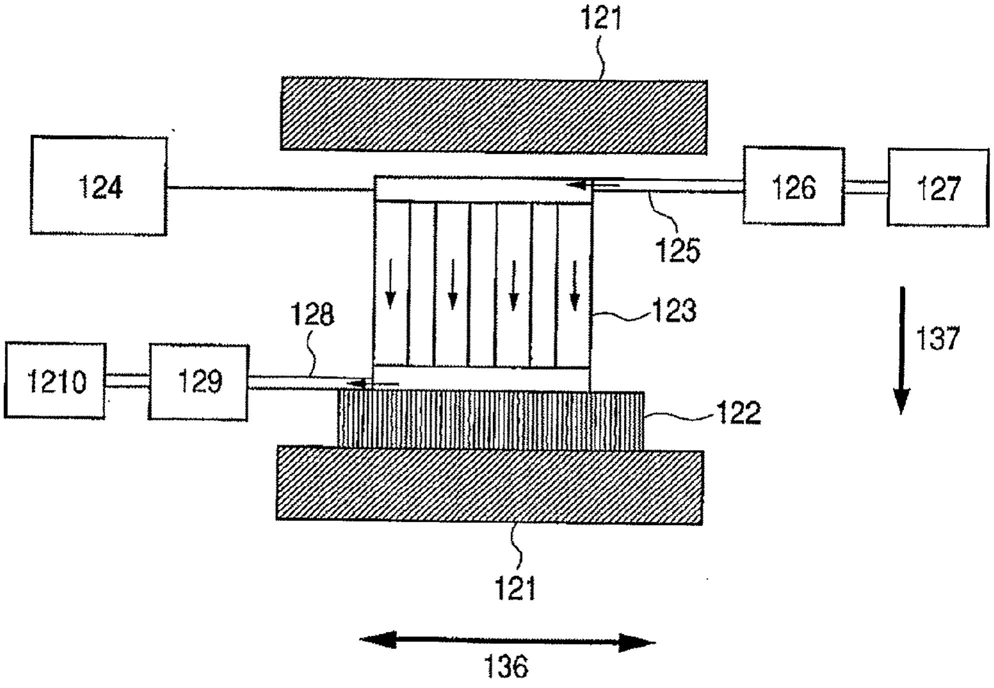
FIG. 12 is a schematic diagram depicting one embodiment of a treatment apparatus of the present invention.

A treatment apparatus of this Example includes a plurality of pairs of a columnar electrode and a cylindrical electrode that surrounds the columnar electrode and achieves the detection of an antigen-antibody reaction product using an enzyme electrode system. FIG. 12 depicts this treatment apparatus. This drawing illustrates one embodiment of a biological material treatment apparatus for stirring a reaction solution in a container by Lorentz force generated by the interaction between an electric current and a magnetic field while performing a reaction step. This FIG. 12 is a conceptual diagram of the cross section of this apparatus in a perpendicular direction.

This apparatus includes a magnet 121, a temperature controller 122, a container 123 for retaining a solution, a power supply 124 (e.g., a potentiostat) and an inlet tube 125 for introducing a solution and a sample. The apparatus also includes a pump 126 and its reservoir 127, an outlet tube 128 for discharging the sample and a pump 129 and its reservoir 1210.

Figure 13:
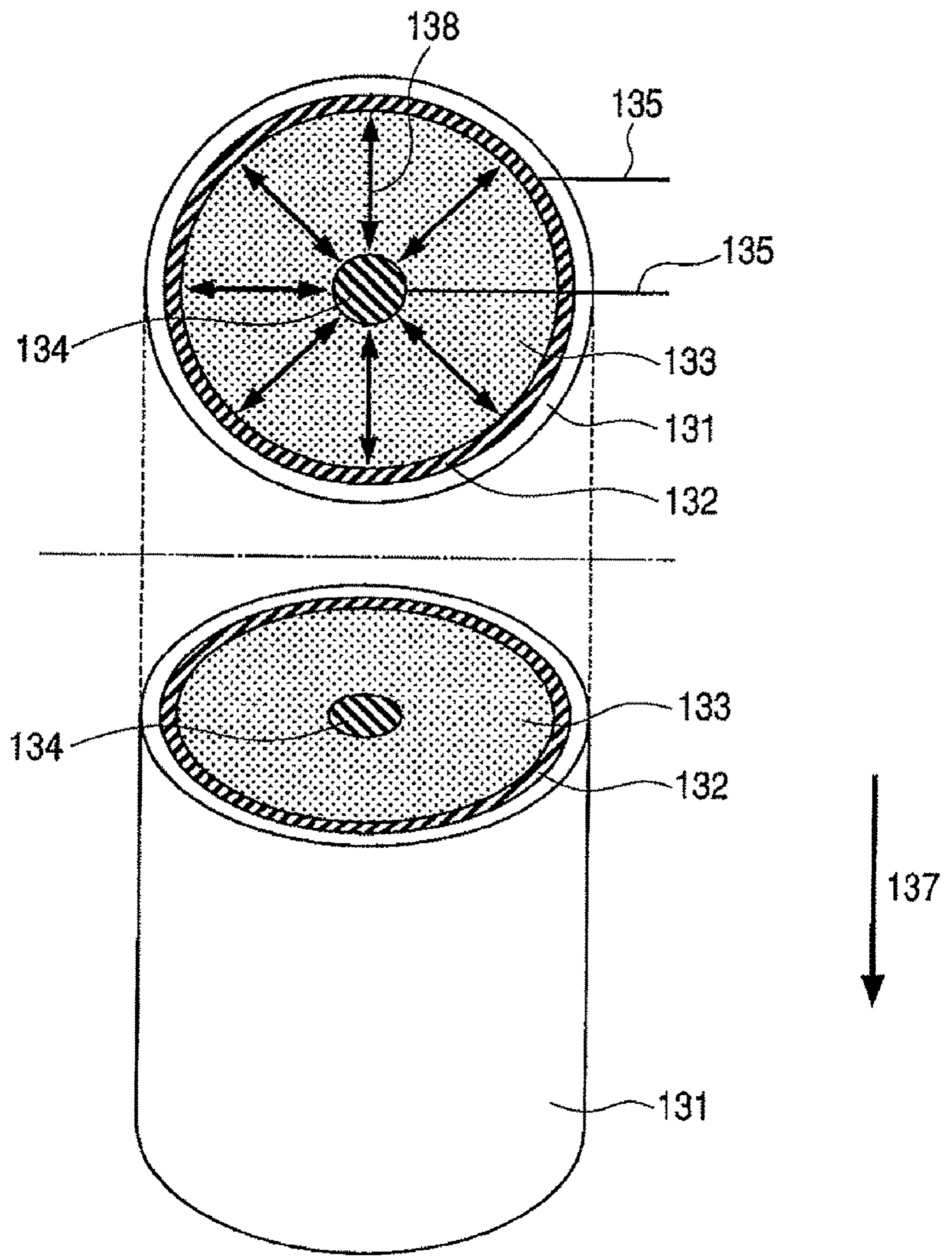
FIG. 13 is a schematic diagram depicting one embodiment of a treatment apparatus of the present invention.

This container 123 for retaining a solution includes a plurality of (here, e.g., four) cylinders. FIG. 13 illustrates a detail diagram of one of the cylinders. The upper diagram of FIG. 13 illustrates the cross section of the container. The lower diagram of FIG. 13 illustrates a perspective view of the container seen from above. The container is surrounded by an outer frame 131. This outer frame is made of, for example, a polyimide resin and is cylindrical in shape. The outer frame is provided in the upper surface thereof with an opening for injecting a sample, an air, a washing solution and so on and provided in the lower surface thereof with an opening for discharging a sample, an air, a washing solution and so on.

A cylindrical electrode 132 is formed on the inner surface of the outer frame. A hollow space 133 is filled with a sample, an air, a washing solution and so on. A columnar electrode 134 is formed in the central portion in the inside of this hollow outer frame. These electrodes are connected to a potentiostat as an outside power supply via leads 135. These electrodes are made of, for example, plated gold (for the electrode 132) or a gold wire (for the electrode 134). A reference electrode made of, for example, a commercially available silver paste for a reference electrode is further formed in the inside by screen printing. The Os complex polymer (solid material) prepared in Preparation Example 1 and a material (anti-IgG; reactive substance) for capturing a biologically relevant substance are immobilized in advance through electrodeposition in the electrodes 134.

An approach for this immobilization was conducted according to the following procedures: a phosphate buffer solution containing 18% by mass of 1 $mg \cdot mL^{-1}$ Os complex polymer was added dropwise onto the electrodes 134. To the electrodes 134, −1.0 V vs. Ag/AgCl was applied for 2 minutes with the potentiostat. Then, the electrodes were washed with deionized water so as to immobilize thereon the Os complex polymer through electrodeposition. After this electrodeposition, a phosphate buffered saline (PBS) containing 1 $mg \cdot mL^{-1}$ avidin was added dropwise onto the electrodes 134. To the electrodes 134, −1.0 V vs. Ag/AgCl was applied for 5 minutes with the potentiostat. Then, the electrodes were washed with deionized water. Furthermore, 6.5 $mg \cdot mL^{-1}$ polyacrylic acid solution for preventing nonspecific adsorption was added dropwise onto the electrodes 134. The electrodes were left standing for 10 minutes and then washed with deionized water and PBS. Commercially available biotin-labeled anti-rabbit IgG (reactive substance) and biotin-labeled anti-goat IgG (reactive substance) were separately dissolved at a concentration of 10 $\mu g \cdot mL^{-1}$ in PBS. Each of these solutions was added dropwise onto two of the four electrodes. After 20-minute reaction at 40° C., the electrodes were washed with deionized water and PBS.

The temperature controller 122 was set to, for example, 40° C. For example, PBS containing target rabbit IgG or goat IgG (biologically relevant substance), 5 mM $K_3[Fe(CN)_6]$ and 5 mM $K_4[Fe(CN)_6]$ was introduced from the reservoir 127 through the inlet tube 125 into the container 123. Then, the electric potential of the electrodes 134 was set to 0.5 V vs. Ag/AgCl. An electric current was applied to the electromagnet so as to apply a magnetic field in a downward direction 137 in FIG. 12. Examples of the magnetic flux density in this case include 1 T. After 10-minute reaction, the application of the electric potential and the magnetic filed was terminated. The inner space of the container was washed with PBS.

Then, an antigen-antibody reaction buffer solution containing 50 nM antibody for detection, for example, 8 μg·mL−1 HRP-labeled anti-rabbit IgG (label for the biologically relevant substance) or HRP-labeled anti-goat IgG (label for the biologically relevant substance), 5 mM $K_3[Fe(CN)_6]$ and 5 mM $K_4[Fe(CN)_6]$ was introduced into the container. Then, the same electric potential and magnetic field as above were applied thereto. After 10-minute reaction at 40° C., the application of the electric potential and the magnetic filed was terminated. The inner space of the container was washed with PBS until the signal of the cyano complex of iron was undetectable.

Then, PBS containing 10 mM $H_2O_2$ was added to the container. The electric potential of the electrodes 134 was set to 0.2 V vs. Ag/AgCl. The stationary electric current was observed. On the other hand, the same procedures as above except for the application of a magnetic field were conducted as a control experiment. This control experiment was used as Comparative Example 3.

In this treatment apparatus, a flow of the oxidation-reduction substances occurs between the electrodes 134 and 132 in a direction perpendicular to the facing direction 136 of the electrodes. This flow undergoes Lorentz force by the interaction thereof with a magnetic field applied in a direction perpendicular to the perpendicular direction (downward direction 137 in FIG. 12; direction parallel to the facing direction). Then, this Lorentz force eventually causes a solution flow. The solution is stirred by this flow.

Figure 14:
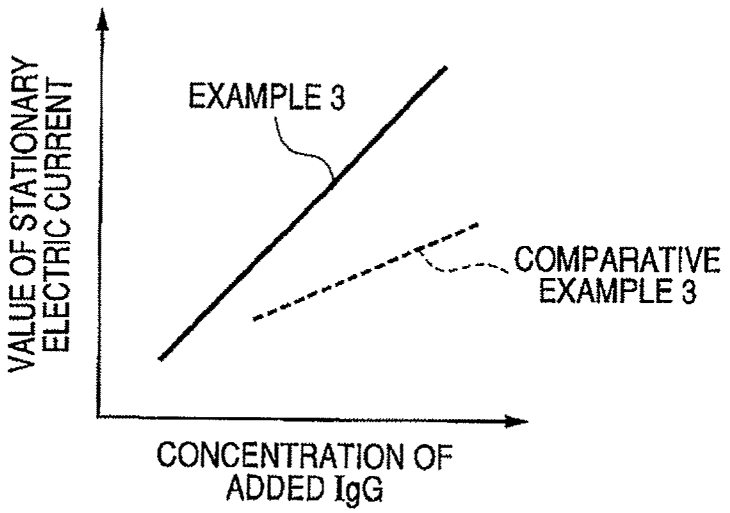
FIG. 14 is a conceptual diagram depicting detection results of Example 3 and Comparative Example 3.

The observation results were plotted with the value of the observed stationary electric current as an ordinate against the concentration of the added IgG as an abscissa. The observation results thus plotted exhibited a tendency illustrated in FIG. 14. Specifically, Example 3 using a magnetic field applied for antigen-antibody reaction resulted in a large value of the stationary electric current observed at the same concentration of the added IgG, as compared with Comparative Example 3 using no applied magnetic field. Moreover, Example 3 achieved detection even at a low concentration of the IgG, as compared with Comparative Example 3. A stationary electric current was observed at the anti-goat IgG-immobilized electrode by supplying goat IgG and at the anti-rabbit IgG-immobilized electrode by supplying rabbit IgG. This principle is the same as in Example 1.

This is probably because the stirring of a solution by MHD effects produced by the interaction between the magnetic field applied during antigen-antibody reaction and the electrolytic current promotes the antigen-antibody reaction.

Example 4

Figure 15:
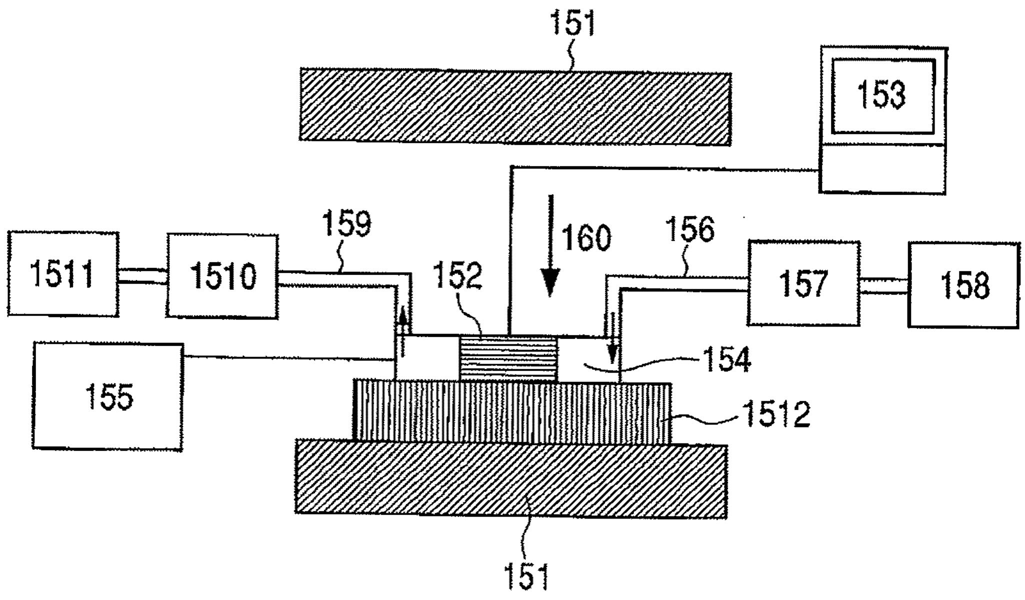
FIG. 15 is a schematic diagram depicting one embodiment of a treatment apparatus of the present invention.

A treatment apparatus of this Example includes two single planar electrodes respectively constituting the inner walls of a container so that these single planar electrodes face each other. This treatment apparatus achieves the transfer of a solution as well as the detection of a biologically relevant substance using a chemiluminescence system. FIG. 15 depicts this treatment apparatus. This drawing illustrates one embodiment of a treatment apparatus for transferring a solution by Lorentz force generated by the interaction between an electric current and a magnetic field while performing a reaction step for detecting a biologically relevant substance in a reaction solution in a container with stirring. This FIG. 15 is a conceptual diagram of the cross section of this apparatus in a perpendicular direction.

This apparatus includes a permanent magnet 151, a photosensor 152 (the photosensor 152 is placed on the front side of the sheet viewed from thin tubes 154 in FIG. 15), an apparatus 153 for performing the operation and analysis of the photosensor 152, and a container 154 for retaining a solution. The apparatus also includes a power supply 155 (e.g., a potentiostat), an inlet tube 156 for introducing a solution and a sample, a pump 157 and its reservoir 158, an outlet tube 159 for discharging the sample, a pump 1510 and its reservoir 1511 and a temperature controller 1512.

Figure 16:
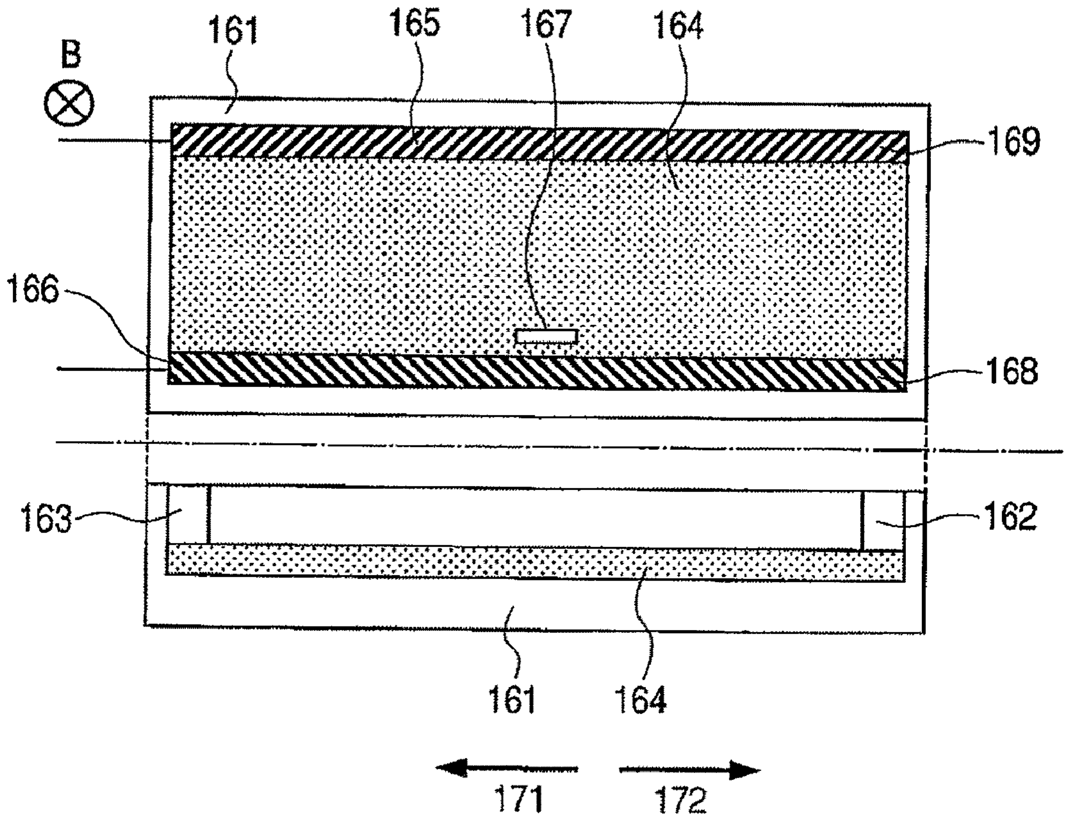
FIG. 16 is a schematic diagram depicting one embodiment of a treatment apparatus of the present invention.

FIG. 16 illustrates a detail diagram of the container 154 for retaining a solution used here. The upper diagram (bottom view) of FIG. 16 illustrates the shape of the inside of the container. The lower diagram of FIG. 16 illustrates a cross-sectional view of the container. The container is surrounded by an outer frame 161. This outer frame is made of, for example, glass and is transparent. The outer frame is provided in the upper surface thereof with an opening 162 for injecting a sample, an air, a washing solution and so on and with an opening 163 for discharging a sample, an air, a washing solution and so on. The outer frame has a hollow structure. A hollow space 164 is filled with a sample, an air, a washing solution and so on. Planar electrodes (anode and cathode) constituting two inner walls 168 and 169 of the container and facing each other are placed in the inner side surface of this hollow outer frame. These electrodes are connected to an outside power supply (e.g. a potentiostat) via leads. These electrodes are made of, for example, ITO (indium tin oxide). A reference electrode 167 made of, for example, a commercially available silver paste for a reference electrode is further formed in the inner bottom surface by screen printing.

A commercially available oligonucleotide for capturing a biologically relevant substance (e.g., 5'-aminated oligonucleotide for target capture; reactive substance) is immobilized on the electrodes 165 and 166 using a silane coupling agent.

This immobilization was conducted as follows: the electrodes were refluxed in anhydrous hexane of 30% 3-aminopropyltriethoxysilane under a nitrogen stream. The electrodes were washed with hexane and dried under a nitrogen stream. Furthermore, 0.1 M phosphate buffer solution (pH 7.4) containing 2.5% by mass of glutaraldehyde was vaporized on the electrodes. After 60-minute reaction at room temperature under a nitrogen stream, the electrodes were washed with water and dried under a nitrogen stream. For example, a phosphate buffered saline (PBS) containing 2 μM 5'-amine-terminated oligonucleotide for capture (reactive substance) having the sequence SEQ ID NO:1 was added dropwise onto the electrodes. After 60-minute reaction at room temperature under a nitrogen stream, the electrodes were washed with water and dried.

The temperature controller 1512 was set to, for example, 53° C. For example, a hybridization buffer solution containing a target oligonucleotide (biologically relevant substance) having the sequence SEQ ID NO:2, 5 mM $K_3[Fe(CN)_6]$ and 5 mM $K_4[Fe(CN)_6]$ was introduced from the reservoir 158 through the inlet tube 156 and the opening 162 into the hollow space 164.

Then, a magnetic field was applied in a downward direction 160 in FIG. 15. Examples of the magnetic flux density in this case include 1 T. The electric potential of the electrode 165 was set to 0.5 V vs. Ag/AgCl. The electric potentials of the electrodes 165 and 166 were switched every 15 seconds.

After 10-minute reaction, the reaction solution was kept at room temperature for 10 minutes. The application of the electric potential was terminated. The inner space of the container was washed with a hybridization buffer solution. Then, a hybridization buffer solution containing 50 nM oligonucleotide for detection, for example, horseradish peroxidase (HRP)-modified oligonucleotide (label for the biologically relevant substance) having the sequence SEQ ID NO:3, 5 mM $K_3[Fe(CN)_6]$ and 5 mM $K_4[Fe(CN)_6]$ was introduced into the hollow space. Then, the same electric potential (including the switching of the electric potentials) as above was applied thereto. After 10-minute reaction at 37° C., the reaction solution was kept at room temperature for 10 minutes. The application of the electric potential was terminated. The inner space of the container was washed 10 times with a hybridization buffer solution.

In this treatment apparatus, a flow of the oxidation-reduction substances occurs in the facing direction of the electrodes. This flow interacts with a magnetic field applied in a direction perpendicular to the facing direction (downward direction 160 in FIG. 15; direction from the front side of the sheet toward the back side thereof or from the back side of the sheet toward the front side thereof in FIG. 16). Then, Lorentz force eventually acts on the solution. This Lorentz force causes a solution flow. The solution is transferred by this flow. A direction in which this solution was transferred could be set to a direction 171 or 172 by reversing an electric potential applied to the electrodes. Simultaneously with this transfer, the stirring of the solution occurred. The biologically relevant substance was detected using this stirring.

Then, a commercially available reagent that caused chemiluminescence in the presence of HRP was added to the container. This light emission was detected by the photosensor 152. On the other hand, the same procedures as above except for the application of a magnetic field were conducted as a control experiment. This control experiment was used as Comparative Example 4.

Figure 17:
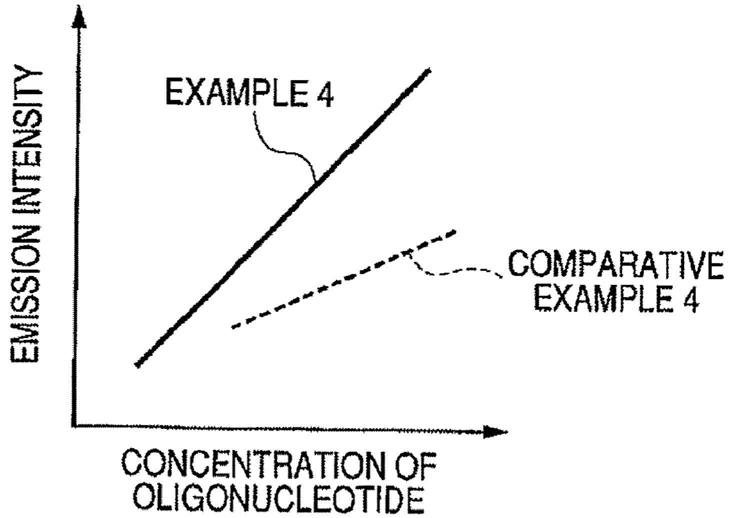
FIG. 17 is a conceptual diagram depicting detection results of Example 4 and Comparative Example 4.

The observation results were plotted with the observed emission intensity as an ordinate against the concentration of the added oligonucleotide as an abscissa. The observation results thus plotted exhibited a tendency illustrated in FIG. 17. Specifically, Example 4 using a magnetic field applied for hybridization resulted in high emission intensity observed at the same concentration of the added oligonucleotide, as compared with Comparative Example 4 using no applied magnetic field. Moreover, Example 4 achieved detection even at a low concentration of the oligonucleotide, as compared with Comparative Example 4. This is because the chemiluminescence reagent emits light by the action of HRP used as a label.

These obtained results are probably because the solution is transferred by MHD effects produced by the interaction between the magnetic field applied during hybridization and the electrolytic current and because the solution is stirred by reversing the electric potentials through switching. As a result, the hybridization reaction is promoted.

Example 5

Figure 18:
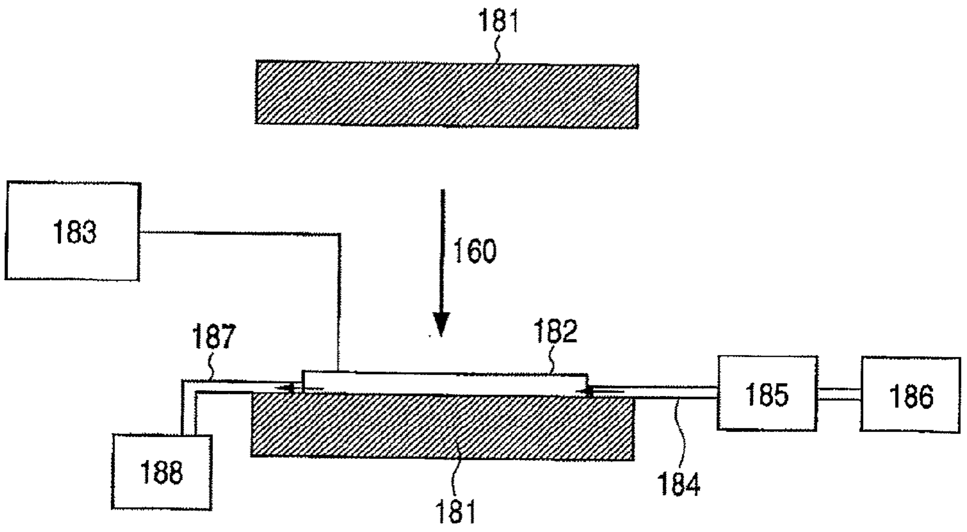
FIG. 18 is a schematic diagram depicting one embodiment of a treatment apparatus of the present invention.

A treatment apparatus of this Example includes two single planar electrodes respectively constituting the inner walls of a thin tube so that these single planar electrodes face each other. This treatment apparatus achieves the transfer of a solution. FIG. 18 is a diagram illustrating one embodiment of this apparatus for transferring a solution in a thin tube by Lorentz force generated by the interaction between an electric current and a magnetic field. This FIG. 18 is a conceptual diagram of the cross section of this apparatus in a perpendicular direction.

This apparatus includes a magnet 181, a thin tube 182 containing electrodes placed therein, a power supply 183 (e.g., a potentiostat), an inlet tube 184 for introducing a solution and a sample, a pump 185 and its reservoir 186, an outlet tube 187 for discharging the sample, and a reservoir 188. In this context, the inner cross section of the thin tube is a square 100 μm on a side. Planar electrodes 193 and 192 constituting two inner walls 195 and 196 of the thin tube and facing each other are placed therein.

Figure 19:
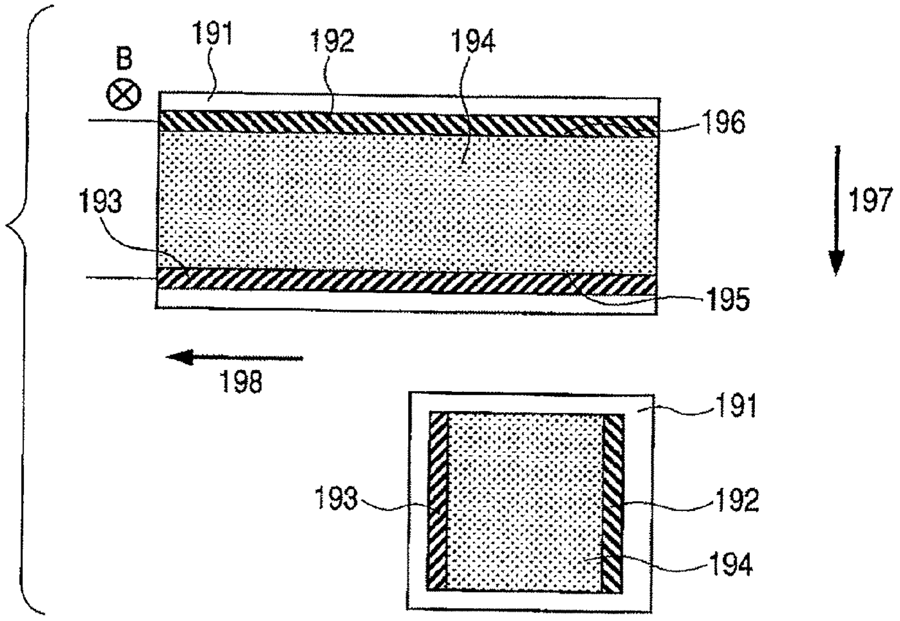
FIG. 19 is a schematic diagram depicting one embodiment of a treatment apparatus of the present invention.

In this context, FIG. 19 illustrates a detail diagram of the thin tube 182 containing electrodes placed therein of this Example. The upper diagram (sectional view of the thin tube viewed from above) of FIG. 19 illustrates the shape of the electrodes in the inside of the thin tube. The lower diagram (sectional view of the thin tube viewed from the side) of FIG. 19 illustrates a side sectional view of the thin tube. The thin tube is surrounded by an outer frame 191. Electrodes (these electrodes are made of a material, e.g., gold) facing each other are provided by plating in the side surfaces of the inner walls of the thin tube. This outer frame is made of, for example, glass. In this context, the thin tube is open-sided (the left and right sides in the sectional view of the thin tube viewed from above) so as to permit the introduction or discharge of a solution and so on. A sample, an air, a washing solution and so on are transferred through a hollow space 194 of the outer frame.

0.1 M phosphate buffer solution (pH 7.0) containing 5 mM $K_3[Fe(CN)_6]$ and 5 mM $K_4[Fe(CN)_6]$ is introduced with the pump 185 from the reservoir 186 through the inlet tube 184 into the hollow space 194 so as to fill the hollow space 194. Then, a magnetic field was applied in a downward direction in FIG. 18. Examples of the magnetic flux density in this case include 1 T. The voltage between the electrodes 192 and 193 was set to 1.0 V (the electrode 192 corresponds to an anode, and the electrode 193 corresponds to a cathode). An electric current was applied to the electromagnet. Then, the amount of the solution discharged through the outlet tube 187 was measured in the reservoir 188. On the other hand, the same procedures as above except for the application of a magnetic field were conducted as a control experiment. This control experiment was used as Comparative Example 5.

In this treatment apparatus, a flow of the oxidation-reduction substances occurs in the facing direction 197 of the electrodes. The flow undergoes Lorentz force by the interaction between an electrolytic current attributed to the flow in this direction and a magnetic field applied in a direction perpendicular to the facing direction 197 (downward direction 160 in FIG. 18; direction from the front side of the sheet toward the back side thereof in FIG. 19). Then, this Lorentz force causes a solution flow in a direction 198. The solution is transferred by this flow.

Figure 20:
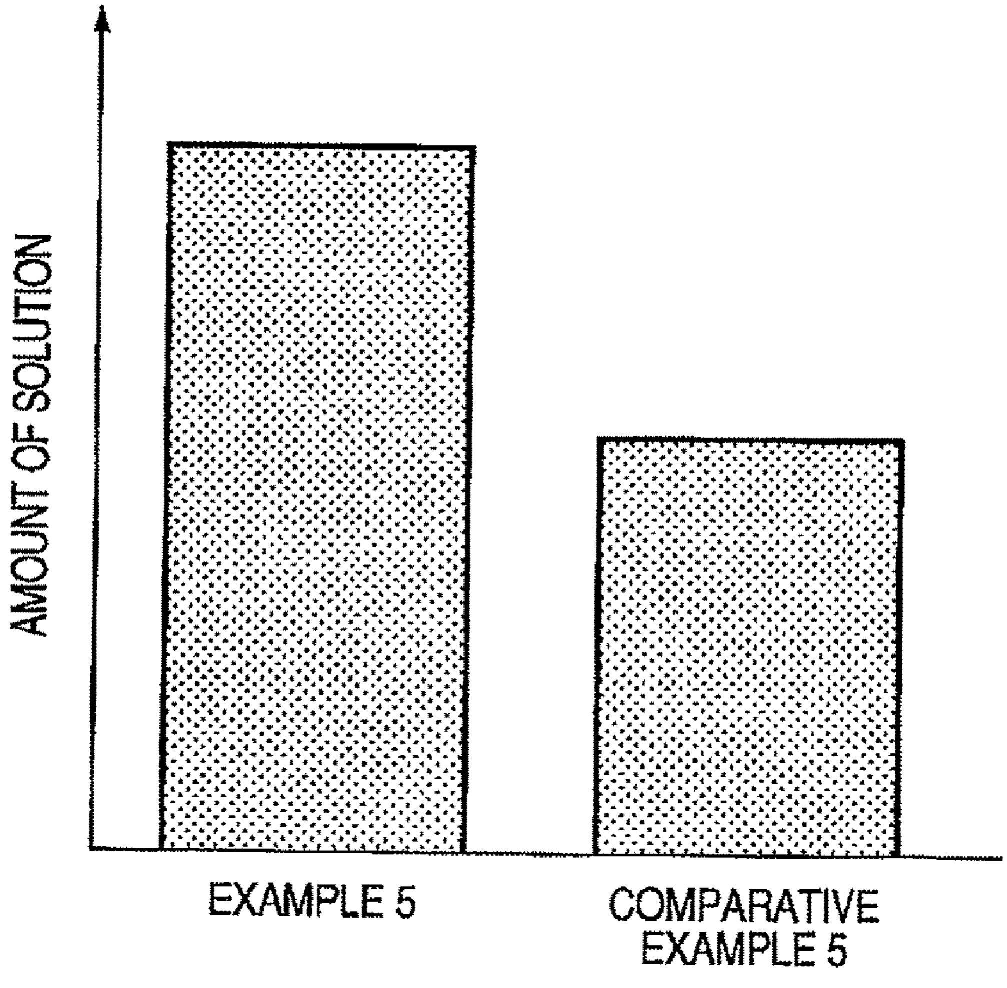
FIG. 20 is a conceptual diagram depicting transferred amounts of Example 5 and Comparative Example 5.

The observation results were plotted with the observed amount of the solution as an ordinate. The observation results thus plotted exhibited a tendency illustrated in FIG. 20. Specifically, in Example 5, the solution is transferred by MHD effects produced by the interaction between the applied magnetic field and the electrolytic current, as compared with Comparative Example 5 using no applied magnetic field. Thus, the solution could be transferred effective in the thin tube usually having large resistance in solution transfer. Furthermore, a solution phase attributed to the MHD effects can be observed even when outside force using the pump is not applied thereto.

The present invention can achieve the effective transfer of a fluid in a thin tube or container or the effective stirring of a solution in a container or thin tube by Lorentz force generated by the interaction between an electric current and a magnetic field. In this procedure, a reaction step of causing the reaction between a biologically relevant substance and a reactive substance may be performed. In such a case, the biologically relevant substance in a sample can be detected effectively. The present invention can provide an apparatus for this purpose. Therefore, the present invention is industrially useful.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-329350, filed Dec. 6, 2006, which is hereby incorporated by reference herein in its entirety.

What is claimed is:

1. A stirring method for stirring a solution in a container, comprising:

preparing the container, the container having a plurality of electrodes, wherein at least one of the plurality of electrodes is circular, wherein a ring electrode surrounds the electrode which is circular, and wherein the ring electrode is provided to detect a target;

introducing the solution into the container; and stirring the solution in the container by Lorentz force generated by an interaction between an electric current mainly generated by an electrolysis reaction of the oxidation-reduction substance at the plurality of electrodes caused by an electric potential or voltage applied from outside of the container to the plurality of electrodes and a magnetic field applied from the outside of the container, wherein the solution comprises an oxidation-reduction substance, and wherein the oxidation-reduction substance is one selected from metal complexes, quinones and heterocyclic compounds.

2. The stirring method according to claim 1, wherein the oxidation-reduction substance is one selected from hexacyanoferrate, ferrocene derivatives, quinones and viologen derivatives.

3. The stirring method according to claim 1, wherein first and second electrodes among the plurality of electrodes are placed in proximity to each other, wherein the first electrode applies a positive charge, and the second electrode applies a negative charge, and wherein the first and second electrodes oxidize or reduce the oxidation-reduction substance.

4. The stirring method according to claim 1, wherein the solution is stirred by rotation caused by the Lorentz force.

* * * * *

```
                         SEQUENCE LISTING

<160> NUMBER OF SEQ ID NOS: 3

<210> SEQ ID NO 1
<211> LENGTH: 34
<212> TYPE: DNA
<213> ORGANISM: Artificial
<220> FEATURE:
<223> OTHER INFORMATION: Reactive material

<400> SEQUENCE: 1

ttttttttt ttcacttcac tttctttcca agag                                34


<210> SEQ ID NO 2
<211> LENGTH: 38
<212> TYPE: DNA
<213> ORGANISM: Artificial
<220> FEATURE:
<223> OTHER INFORMATION: Living organism-related material

<400> SEQUENCE: 2

aggcatagga cccgtgtcct cttggaaaga aagtgaag                            38


<210> SEQ ID NO 3
<211> LENGTH: 18
<212> TYPE: DNA
<213> ORGANISM: Artificial
<220> FEATURE:
<223> OTHER INFORMATION: Label of living organism-related material

<400> SEQUENCE: 3

gacacgggtc ctatgcct                                                  18
```